(12) United States Patent
Koch et al.

(10) Patent No.: US 7,371,737 B2
(45) Date of Patent: May 13, 2008

(54) 2-SUBSTITUTED-6-TRIFLUOROMETHYL PURINE DERIVATIVES WITH ADENOSINE-$A_3$ ANTAGONISTIC ACTIVITY

(75) Inventors: Melle Koch, Weesp (NL); Jacobus A. J. den Hartog, Weesp (NL); Gerrit-Jan Koomen, Weesp (NL); Martinus J. Wanner, Weesp (NL); Roelof W. Feenstra, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 17 days.

(21) Appl. No.: 11/219,818

(22) Filed: Sep. 7, 2005

(65) Prior Publication Data

US 2006/0052331 A1 Mar. 9, 2006

Related U.S. Application Data

(60) Provisional application No. 60/608,147, filed on Sep. 9, 2004.

(51) Int. Cl.
*A01N 43/04* (2006.01)
*A01N 43/90* (2006.01)
*A61K 31/70* (2006.01)
*C07H 19/00* (2006.01)
*C07D 473/00* (2006.01)

(52) U.S. Cl. ............... 514/45; 514/263.1; 536/27.1; 544/264

(58) Field of Classification Search ............... 514/45, 514/263.1; 536/27.1; 544/264
See application file for complete search history.

(56) References Cited

FOREIGN PATENT DOCUMENTS

| EP | 0 354 180 A2 | 2/1990 |
|---|---|---|
| JP | 2004-217582 | 5/2004 |
| WO | WO 02/31176 A1 | 4/2002 |
| WO | WO 2004/069185 A2 | 8/2004 |
| WO | WO 2006/027366 A1 | 3/2006 |

OTHER PUBLICATIONS

Francis, J.E., et al., "A general synthesis of 5,7-diaminoimidazo[4,5-*b*]pyridine ribosides ("2-amino-1-deazaadenosines") from 5-amino-4-imidazolecarboxamide riboside (AICA riboside)," Canadian J. Chem. 70, pp. 1288-1295, (1992).
Camaioni, E., et al., "New Substituted 9-Alkylpurines as Adenosine Receptor Ligands," Bioorganic & Medicinal Chemistry 6(5), pp. 523-533 (1998).
Wanner, M.J., et al., "2-Nitro Analogues of Adenosine and 1-Deazaadenosine: Synthesis and Binding Studies at the Adenosine $A_1$, $A_{2A}$ and $A_3$ Receptor Subtypes," Bioorganic & Medicinal Chemistry Letters, vol. 10, No. 18, pp. 2141-2144 (2000).
Sullivan, G.W., et al., "Cyclic AMP-dependent inhibition of human neutrophil oxidative activity by substituted 2-propynlcyclohexyl adenosine $A_{2A}$ receptor agonists," British Journal of Pharmacology, vol. 132, No. 5, (Mar. 2001), pp. 1017-1026 (XP002322595).
Niiya et al., "2-(N'-Alkylidenehydrazino) Adenosines: Potent and Selective Coronary Vasodilators," Journal of Medicinal Chemistry, vol. 35, No. 24, (1992), pp. 4557-4561.
Medicinal Chemistry: "Principles and Practice," (1994), ISBN 0-85186-494-5, Ed.: F.D. King, p. 215.
Stella, J., "Prodrugs As Therapeutics," Expert Opin. Ther. Patents, 14(3), pp. 277-280 (2004).
Ettmayer, P., et al., "Lessons Learned from Marketed and Investigational Prodrugs," J. Med. Chem., 47 (10), pp. 2393-2404, (2004).
Cristalli et al., "Improved Synthesis and Antitumor Activity of 1-Deazaadenosine" J. Med. Chem. (1987), 30, pp. 1686-1688.
Itoh et al., "Studies on the Chemical synthesis of Potential Antimetabolites Regioselective Introduction of a Chlorine Atom into the Imidazo [4,5-*b*]pyridine Nucleus (1)," J. Heterocyclic Chem. (1982), 19, pp. 513-517.
Deghati et al., "Mild and Regioselective Nitration of 1-deazapurine Nucleosides using TBAN/TFAA," Tetrahedron Letters (2000), 41, pp. 569-573.
Wanner et al., "Synthesis and Properties of 2-nitrosoadenosine," J. Chem. Soc. Perkin Trans 1, (2001), pp. 1908-1915.
Townsend, A., et al., "A Threonine Residue in the Seventh Transmemebrane Domain of the Human $A_1$ Adenosine Receptor Mediates Specific Agonist Binding," Biol. Chem., 269, p. 2373-2376 (1994).
Luthin, D.R., et al., "Characterization of Two Affinity States of Adenosine $A_{2a}$ Receptors with a New Radioligand, 2-[2-(4-Amino-3-[$^{125}$I]iodophenyl)ethylamino]adenosine," Mol. Pharmacol., 47, p. 307 (1995).
Stehle, J.H., et al., "Molecular Cloning and Expression of the cDNA for a Novel $A_2$-Adenosine Receptor Subtype," Mol. Endocrinol., 6, p. 384, (1992).

(Continued)

*Primary Examiner*—Shaojia Anna Jiang
*Assistant Examiner*—Traviss C. McIntosh, III
(74) *Attorney, Agent, or Firm*—Finnegan, Henderson, Farabow, Garrett & Dunner, L.L.P.

(57) ABSTRACT

The present invention relates to 2-substituted-6-trifluoromethyl purine derivatives as selective adenosine antagonists, in particular adenosine-$A_3$ receptor antagonists, to methods for the preparation of these compounds and to novel intermediates useful for the synthesis of said purine derivatives.

The compounds have the general formula (1)

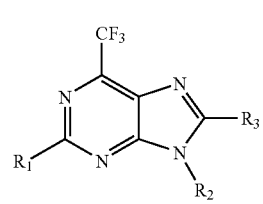

(1)

wherein the symbols have the meanings given in the specification.

15 Claims, No Drawings

OTHER PUBLICATIONS

Salvatore, C.A., et al., "Molecular Cloning and Characterization of the Human A₃ Adenosine Receptor," Proc. Natl. Acad. Sci. USA, 90, pp. 10365-10369 (1993).

Hess, S., "Recent Advances in Adenosine Receptor Antagonist Research", Expert Opin. Ther. Patents, 11, pp. 1547-1562, (2001).

Jacobsen, M.A., "Adenosine Receptor Agonists," Expert Opin. Ther. Patents, 12(4), pp. 489-501, (2002).

Cristalli, G., et al., II "Purine and Deazapurine n=Nucleosides: Synthetic Approaches, Molecular Modeling and Biological Activity," Farmaco, 58, pp. 193-204, (2003).

Klotz, K., et al., "9-Ethyladenine Derivatives as Adenosine Receptor Antagonists: 2- and 8-substitution results in distinct selectivities, Naunyn-Schmiedeberg's Archives of Pharmacology," 367, pp. 629-634 (2003).

Ginger-Sorolla, A., et al., "Fluorine-containing and Purines: Synthesis and Properties of Trifluoromethyl Pyrimidines and Purines[1]," JACS 80, pp. 5744-5752, (1958).

Kaiser, C., et al., "A Synthesis of 2-Amino-6-trifluoromethyl-purine," J. Org. Chem. 24, pp. 113-114, (1959).

Nagano, H., et al., "Fluorine-Containing Potential Anticancer Agents. II. [1a]Syntheses of Some Trifluoromethylpurines and Trifluoromethylthiazolopyrimidines [1b]," J. of Med. Chem, Amer. Chem. Soc., vol. 7, No., pp. 215-220, (1964).

Kobayashi, Y., et al. "Studies on Organic Fluorine Compounds. Part 35.[1] Trifluoromethyl-ation of Pyrimidine- and Purine-nucleosides with Trifluoromethyl-Copper Complex," J. Chem. Soc. Perkin 1, pp. 2755-2761, (1980).

Green, A.R., et al., "The Effect of the C-6 Substituent on the Regioselectivity of N-Alkylation of 2-Aminopurines," Tetrahedron vol. 46, No. 19 pp. 6903-6914, (1990).

Hockova, D., et al., "Synthesis and Cytostatic Activity of Nucleosides and Acyclic Nucleoside Analogues Derived from 6-(Trifluoromethyl)purines," Tetrahedron 55, pp. 11109-11118, (1990).

Veliz, E.A., et al. "Synthesis and Analysis of RNA Containing 6-Trifluoromethylpurine Ribonucleoside," Organic Letters, vol. 3, No. 19, pp. 2969-2972 (2001).

Hocek, M., et al., "Perfluoraoalkylation of 6-Iodopurines By Trimethyl(Perfluoroalkyl)Silanes. Synthesis of 6-(Perfluoroalkyl)Purine Bases, Nucleosides and Acyclic Nucleotide Analogues," Collection of Czechoslovak Chemical Communications, 64, p. 229-241, (1999).

Ueeda, M. et al., "2-Alkoxyadenosines: Potent and Selective Agonists at the Coronary Artery $A_2$ Adenosine Receptor," J. Med. Chem., 34, pp. 1334-1339, (1991).

Rodenko, B., et al., "Solid Phase Synthesis of $C2,N^6$-disubstituted adenosine analogues," J. Chem. Soc., Perkin Trans., 1, (2002), pp. 1247-1252.

Rodenko, B., et al., "The Mechanism of Selective Purine C-Nitration Revealed: NMR Studies Demonstrate Formation and Radical Rearrangement of an N7-Nitramine Intermediate," J. A.M. Chem. Soc., (2005), 127, pp. 5957-5963.

Gao Z.G., et al., "2-Substituted Adenosine Derivatives: Affinity and Efficacy at Four Subtypes of Human Adenosine Receptors," Biochemical Pharmacology 68 (2004) pp. 1985-1993.

Wanner, M.J., et al., "2-Nitro Analogues of Adenosine and 1-Deazaadenosine: Synthesis and Binding Studies at the Adenosine $A_1$, $A_{2A}$ and $A_3$ Receptor Subtypes," Bio. & Med. Chem. Letter, 10, pp. 2141-2144 (2000).

Search Report for PCT/EP2005/054405 dated Jan. 2, 2006.

Search Report for PCT/EP2005/054404 dated Jan. 16, 2006.

Written Opinion for PCT/EP2005/054404.

Copending U.S. Appl. No. 11/219,817, filed Sep. 7, 2005.

English language Abstract for JP 2004-217582.

2-SUBSTITUTED-6-TRIFLUOROMETHYL PURINE DERIVATIVES WITH ADENOSINE-A$_3$ ANTAGONISTIC ACTIVITY

CROSS REFERENCE TO RELATED APPLICATION

This application claims the benefit of U.S. Provisional Application No. 60/608,147, filed Sep. 9, 2004, the content of which is incorporated herein by reference.

The present invention relates to 2-substituted-6-trifluoromethyl purine derivatives as selective adenosine antagonists, in particular adenosine-A$_3$ receptor antagonists, to methods for the preparation of these compounds and to novel intermediates useful for the synthesis of said purine derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which adenosine-A$_3$ receptors are involved, or that can be treated via manipulation of those receptors.

At present, four types of adenosine receptors have been identified and designated A$_1$, A$_{2A}$, A$_{2B}$ and A$_3$ respectively. All four belong to the super-family of seven transmembrane G-protein coupled receptors. Adenosine receptors are ubiquitous and involved in a great variety of biological processes. Thus, during the past decades the therapeutic potential of adenosine receptor ligands has resulted in a substantial research interest.

Several studies indicate that adenosine A$_3$ receptors may play a basic role in different pathologies such as inflammation and neurodegeneration, ischemic brain damage, cardiac ischemia, hypotension, ischemic heart pre-conditioning, asthma and cancer. (P. G. Baraldi et al., European Journal of Medicinal Chemistry, 38, 367-382, 2003, and references cited therein). In the (patent) literature, adenosine A$_3$ receptor antagonists have been claimed to be useful for the treatment of acute and chronic pain, inflammatory diseases including, arthritis, multiple sclerosis, asthma and psoriasis; gastrointestinal disorders such as ulcers, inflammatory bowel disease (Crohn's disease) and ulcerative colitis; allergic responses such as eczema, atopic dermatitis and rhinitis; cardio-vascular disorders such as myocardial infarction, arrhythmias, hypertension, thrombosis, anaemia, arteriosclerosis, angina pectoris, cutaneous diseases such as urticaria, lupus erythematosus and pruritus; opthalmological disorders like glaucoma; respiratory disorders including chronic obstructive pulmonary disease, bronchitis and cystic fibrosis; central nervous system disorders including various forms of epilepsy, stroke, depression, sleep apnoea; disorders characterized by impairment of cognition and memory such as Alzheimer's disease, Creutzfeldt-Jacob disease, Huntington's disease, Parkinson's disease, neurorehabilitation (post-traumatic brain lesions); acute brain or spinal cord injury; diabetes, osteoporosis, diseases of the immune system, various carcinomas and leukemia, bacterial and viral infections.

Selective adenosine A$_3$ receptor antagonists are known. Diverse lead structures belonging to the classes of flavanoids, 1,4-dihydropyridines, pyridines, pyranes, pyrazolotriazolopyrimidines, triazoloquinazolines, isoquinolines, quinazolines and xanthines have been reviewed by S. Hess (Expert Opin. Ther. Patents, 11, 1547-1562, 2001) and M. A. Jacobson (Expert Opin. Ther. Patents, 12(4), 489-501, 2002). Despite the fact that during the quest for potent and selective adenosine receptor ligands the purine skeleton of the natural ligand adenosine (6-amino-9-β-D-ribofuranosyl-9H-purine) was intensely used as a starting point there are just two publications describing adenosine derivatives as adenosine antagonists with selectivity for the A$_3$ receptor subtype: G. Cristalli et al. (II Farmaco, 58, 193-204, 2003) and K. Klotz et al. (Naunyn-Schmiedeberg's Archives of Pharmacology, 367, 629-634, 2003), describing 9-ethyl-8-phenethylethynyl-9H-adenine as a selective adenosine A$_3$ receptor antagonist.

Replacement of the (natural) 6-amino group in the adenosine skeleton by the CF$_3$-moiety was tried by different research groups. Because of severe technical limitations, these efforts led to the synthesis of a very limited set of analogs only (Purines: Ciba Found Symp, Chem & Biol, 3, 1957; JACS 80, 5744, 1958; J Org Chem 24, 113, 1959; J Med Chem 7. 215, 1964; J Chem Soc Perkin 1, 2755, 1980; Tetrahedron 46, 6903, 1990 and 55, 11109, 1999; Coll Czech Chem Comm 64, 229, 1999 and 65, 1357, 2000; Org Lett, 3, 2969, 2001 and WO2002031176). No adenosine receptor interaction data were reported for these compounds. The same is true for the 6-perfluoroalkyl purines described by M. Hocek et al. (Collection of Czechoslovak Chemical Communications, 64, 229-241, 1999), and D. Hockova et al. (Tetrahedron, 55, 11109-11118, 1999). In fact of all compounds described, only 6-trifluoromethyl-9-β-D-ribofuranosyl purine was found to have cytostatic activity. Close structural analogs were all inactive, and no mention was made of possible interaction with adenosine receptors. The Japanese patent application JP 2004 217582 describes purine derivatives as TNF$_\alpha$ antagonists. Two of the examples contained therein have a 6-trifluoromethyl group, but nothing is disclosed about adenosine receptors. H. Nagano et al. describe yet another group trifluromethylpurines as potential anti-tumor agents (J. Med. Chem., 7, 215-220, 1964). None of these compounds showed any activity at all, and the document is silent about adenosine receptors. E. Camaione et al describe a series of 9-alkyl (ethyl) purines as adenosine receptor ligands (Bioorganic & Medicnal Chemistry, 6, 523-533, 1998). All of the compounds disclosed however, are selective adenosine A$_{2A}$ receptor antagonists. None is selective for adenosine A$_3$ receptors. The same applies to the 2-alkoxyadenosines described by M. Ueeda et al (J. Med. Chem., 34, 1334-1339, 1991): all compounds described are adenosine A$_2$ selective. Likewise, the adenosine analogs disclosed in WO 2004/069185 are all selective adenosine A$_1$ (partial) agonists.

In summary: the available literature does not provide incentives towards the design as selective adenosine A$_3$ receptor antagonists of the uniquely substituted purine derivatives of the present invention, in particular with respect to the trifluoromethyl moiety at position 6 of the purine core.

During exploration of the synthetic possibilities of the purine skeleton it was found that introduction of a nitro group at the 2-position followed by insertion of a trifluoromethyl group at position C6, resulted in activated intermediates that allow easy replacement of the 2-nitro group by many different types of nucleophiles. In this way a fruitful combination of two hitherto technically hard conversions was realized.

Surprisingly the novel compounds obtained by this new synthetic route, turned out to be adenosine receptor ligands (in contrast to previously described 6-$CF_3$ derivatives), more specifically: adenosine-$A_3$ receptor selective antagonists. The invention relates to compounds of the general formula (1):

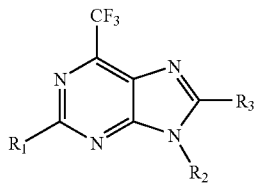

(1)

wherein $R_1$ represents —[X—$(CH_2)_n]_m$—Y, in which formula X is either NH or oxygen, n is 0, 1, 2 or 3, m is 0 or 1, and Y is an optionally substituted 5- or 6-membered aromatic or non-aromatic ring, containing 0, 1 or 2 heteroatoms selected from N, O and S, or $R_1$ represents a nitro goup, $R_2$ is hydrogen, $C_{1-3}$-alkyl, ribose, —$CH_2$—O—CO—O-t-butyl or aryl-($C_{1-3}$)alkyl, $R_3$ represents hydrogen, halogen, $NH_2$, —NH—$(C_{1-6})$ alkyl, —N-di$(C_{1-6})$alkyl, —NH-cyclo$(C_{3-8})$alkyl, $C_{2-4}$-alkenyl(hetero)aryl or $C_{2-4}$-alkynyl(hetero)aryl, of which the hetero-atoms are selected from N, O, and S, and which (hetero)aryl groups may be optionally substituted, or $R_3$ represents an optionally substituted 5- or 6-membered aromatic or non-aromatic ring, containing 0, 1 or 2 hetero-atoms selected from nitrogen, oxygen and sulphur, and tautomers, stereoisomers, prodrugs and salts thereof. Such compounds are new and are adenosine-$A_3$ receptor antagonists.

The invention relates to racemates, mixtures of diastereomers as well as the individual stereoisomers of the compounds having formula (1). The invention also relates to the E isomer, Z isomer and E/Z mixtures of compounds having formula (1).

Throughout this specification the generally accepted atom numbering system of the purine skeleton is used:

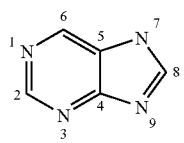

When compounds are described that are substituted with ribose on nitrogen atom 9 (thus compounds of formula (1) in which $R_2$ is ribose), the exact meaning is 9-β-ribofuranosyl, having the following structural characteristics:

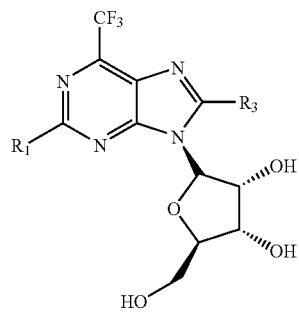

Furthermore, in the description of the substituents the abbreviation '$C_{1-3}$-alkyl' means 'methyl, ethyl, n-propyl or isopropyl'. 'Optionally substituted' means that a group may or may not be further substituted by one or more groups selected from alkyl, alkenyl, alkynyl, aryl, fluoro, chloro, bromo, hydroxyl, alkyloxy, alkenyloxy, aryloxy, acyloxy, amino, alkylamino, dialkylamino, arylamino, thio, alkylthio, arylthio, cyano, oxo, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulphur. Within the context of the explanation of 'optionally substituted', 'alkyl' means $C_{1-3}$-alkyl, 'alkenyl' means $C_{1-3}$-alkenyl, 'alkynyl' means $C_{1-3}$-alkynyl, 'acyl' means $C_{1-3}$-acyl and 'aryl' means furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 1,3,5-triazynyl, phenyl, indazolyl, indolyl, indolizinyl, isoindolyl, benzi[b]furanyl, benzo[b]thiophenyl, benzimidazolyl, benzthiazolyl, purinyl, quinolynyl, isochinolyl, chinolyl, phtalazinyl, quinazolinyl, quinoxalinyl, 1,8-naphthyridinyl, pteridinyl, naphthyl or azulenyl, preferably phenyl, pyridyl or naphthyl. Optional substituents may themselves bear additional optional substituents. Preferred optional substituents include $C_{1-3}$ alkyl such as for example methyl, ethyl, and trifluoromethyl, fluoro, chloro, bromo, hydroxyl, $C_{1-3}$ alkyloxy such as for example methoxy, ethoxy and trifluoromethoxy, and amino.

Prodrugs of the compounds mentioned above are in the scope of the present invention.

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", Expert Opin. Ther. Patents, 14(3), 277-280, 2004; P. Ettmayer et al., "Lessons learned from marketed and investigational prodrugs", J. Med. Chem., 47, 2393-2404, 2004).

Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

The invention particularly relates to compounds of formula (1) in which:

$R_1$ represents —[X—$(CH_2)_n$]$_m$—Y, in which formula X is either NH or oxygen, n is 1 or 2, m is 0 or 1, and Y is an optionally substituted 6-membered aromatic or non-aromatic ring, containing 0, 1 or 2 hetero-atoms selected from N and O, or $R_1$ represents a nitro goup, $R_2$ represents hydrogen, methyl, ribose or —$CH_2$—O—CO—O-t-butyl, $R_3$ represents hydrogen, halogen, —NH-cyclopentyl, ethenylphenyl or ethynylphenyl, which phenyl groups may be optionally substituted with a $CF_3$ group, or $R_3$ represents an optionally substituted 5- or 6-membered aromatic or non-aromatic ring, containing 0, 1 or 2 hetero-atoms selected from nitrogen, oxygen and sulphur, and tautomers, stereoisomers, prodrugs and salts thereof.

More in particular, the invention relates to compounds of formula (1) in which $R_1$ represents —[X—$(CH_2)_n$]$_m$—Y, in which formula X is either NH or oxygen, n is 1 or 2, m is 0 or 1, and Y is an optionally hydroxylated 6-membered aromatic or non-aromatic ring, containing 0 or 1 N-atoms, $R_2$ represents hydrogen, methyl, ribose or —$CH_2$—O—CO—O-t-butyl, $R_3$ represents hydrogen, halogen, —NH-cyclopentyl, ethenylphenyl or ethynylphenyl, which phenyl groups may be optionally substituted with a $CF_3$ group, or $R_3$ represents an optionally substituted 5- or 6-membered aromatic or non-aromatic ring, containing 0, 1 or 2 hetero-atoms selected from nitrogen, oxygen and sulphur, and tautomers, stereoisomers, prodrugs and salts thereof.

The most preferred compounds are those of formula (1) in which:

$R_1$ represents —[X—$(CH_2)_n$]$_m$—Y, in which formula X is NH, n is 1 or 2, m is 1, and Y is an optionally hydroxylated phenyl group, $R_2$ represents hydrogen, ribose or —$CH_2$—O—CO—O-t-butyl, $R_3$ represents hydrogen, and tautomers, stereoisomers, prodrugs and salts thereof.

General Aspects of Syntheses

The synthesis of compounds having formula (1) is outlined in schemes 1 and 2

Scheme 1.

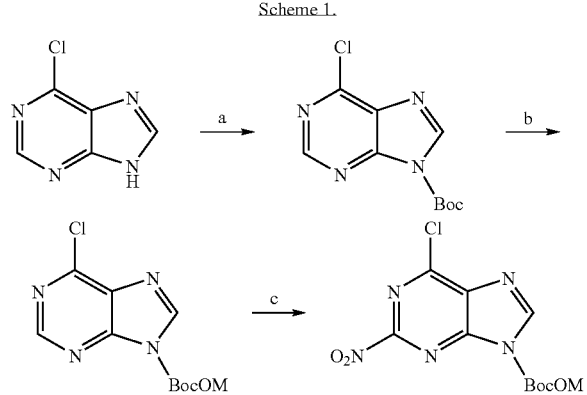

BocOM = 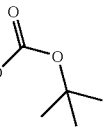

(a) Boc$_2$O, DMAP, rt; (b) para-formaldehyde, DMAP; (c) TBAN/TFAA

The introduction of substituents on the 2- and 6-position of purines is generally achieved via nucleophilic displacement of 2,6-dihalogenated purine derivatives. The introduction of a nitro group at the 2-position by nitration with tetrabutylammoniumnitrate and trifluoroacetic anhydride was recently described (Deghati, Wanner and Koomen, "Regioselective nitration of purine nucleosides: synthesis of 2-nitroadenosine and 2-nitroinosine". Tetrahedron Letters 2000, 41, 1291-1295.) The 2-nitro group greatly enhanced the electrophilicity of the purine C-6 position. The introduction of a trifluoromethyl group on purine C6 is greatly facilitated by the C2 nitro substituent. The reaction can already be achieved at –20° C., while other protocols need highly elevated temperature and catalysts (Hocek, Collection of Czechoslovak Chemical Communications, 1999, 64(2), 229-241). The functionalization of C2 with nucleophiles is highly enhanced by the C6 $CF_3$-substituent. Introduction of nucleophiles can proceed at temperatures varying from 0° to 40° C.

The N9 position can be functionalised with different alkyl or arylalkyl groups via standard alkylation or Mitsunobu conditions.

After introduction of a halogen (I, Br) substituent at position C8 of the purine system, these compounds can be further functionalised by adding nucleophiles. Palladium catalysed coupling procedures (Sonogashira, Stille, Suzuki, Buchwald-Hartwig) allow for a broad range of carbon and heteroatom nucleophiles that can be introduced on the 8 position of the halo-purines.

Scheme 2.

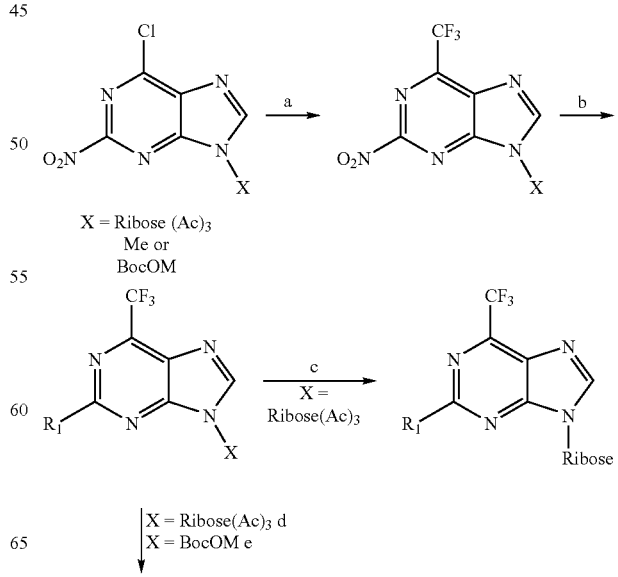

-continued

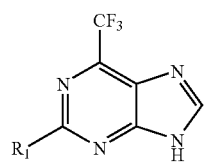

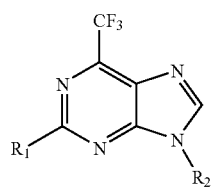 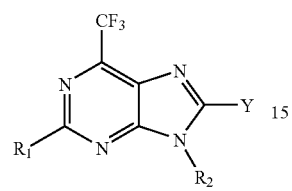

Y = I or Br

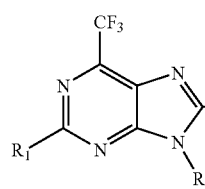 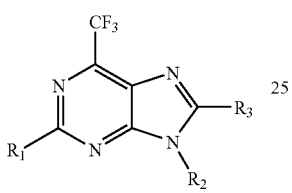

(a) trifluoromethylation; (b) nucleophilic substitution; (c) NH₃ (d) TFA;
(e) NaOMe; (f) alkylation (g) halogenation; (h) amination; (i) Pd coupling The present invention therefore also relates to a process for the preparation of compounds as described above, comprising the steps of:

(a) trifluoromethylation of a compound of the general formula (3):

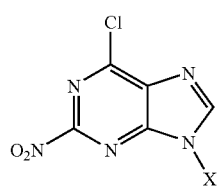

(3)

wherein X is tri-O-acetate-ribose, methyl or —CH₂—O—C(O)O-tBu;

resulting in a compound of the general formula (4):

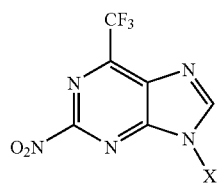

(4)

(b): nucleophilic substitution of the nitro group by in compound (4) to yield a compound with the general formula (5):

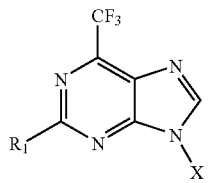

(5)

wherein $R_1$ has the meanings as given in claim 1, and, (c1): with compounds in which X=tri-O-acetate-ribose, hydrolysing the compound of formula (5) to yield the corresponding compound with the general formula (1) with a 9-ribose substituent:

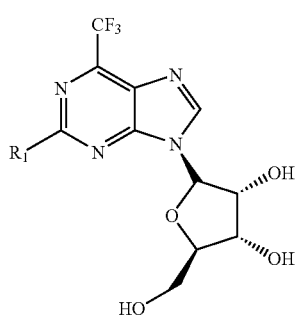

(1)

or:

(c2): with compounds in which X=tri-O-acetate-ribose, treating the product with a strong organic acid to yield a compound of the general formula (6):

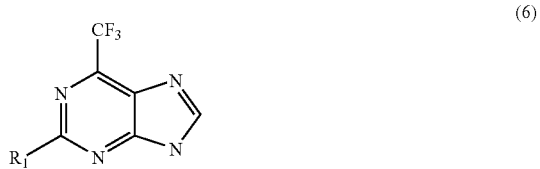

(6)

or:

(c3): by treating a compound of form (5) in which X=—CH₂—O—C(O)O-tBu with as strong base to yield a compound of the general formula (6), (d): alkylation of a compound of formula (6) to yield a compound of general formula (7):

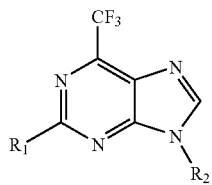

(7)

in which $R_2$ has the meanings as given above, (e) halogenation of the compound with formula (7) to yield a compound of the general formula (8):

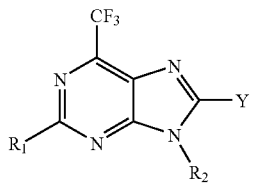

(8)

wherein Y is either Br or I (iodine), and (f): either standard amination or alkylation procedures to result in a compound of the general formula (1) as described above:

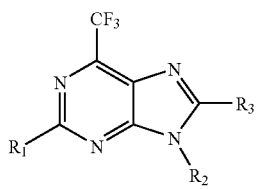

(1)

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

The trifluoromethylation step (a) is preferably carried out by adding $CF_3TMS$ to a suspenstion of the compound of formula (3) and CsF in dry THF.

The nucleophilic substitution reaction on compound (4) is preferably carried out by dissolving the compound with the chosen amine in the presence of triethylamine.

The hydrolysis reaction (c1) is preferably carried out by treating the compound of formula (5) wherein X=tri-O-acetate-ribose with a 1:1 NH3 solution and methanol.

The reaction (c2) is preferably performed with trifluoroacetic acid.

The strong base in reaction (c3) is preferably MeONa in methanol.

The alkylation reaction (d) of the compound of formula (6) can be performed by standard alkylation procedures or under Mitsunobu conditions.

The halogenation reaction (e) is preferably carried out by cooling the solution of the compound with formula (7) in THF followed by addition of n-BuLi and $Br_2$ or $I_2$.

In case of an amination the reaction (f) is performed by standard procedures, in case of an alkylation the reaction is preferably performed by Pd coupling procedure.

Pharmaceutically acceptable salts may be obtained using standard procedures well known in the art, for example by mixing a compound of the present invention with a suitable acid, for instance an inorganic acid such as hydrochloric acid, or with an organic acid.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. The invention also includes the preparation or manufacture of said pharmaceutical compositions.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

The adenosine-$A_3$ receptor antagonistic properties of the compounds of the invention were determined using the methods outlined below.

In Vitro Affinity for Human Adenosine-$A_3$ Receptors

Affinity of the compounds for human adenosine-$A_3$ receptors was determined using the receptor binding assay described by C. A. Salvatore et al.: "*Molecular cloning and characterization of the human $A_3$ adenosine receptor*", Proc. Natl. Acad. Sci. USA, 90, 10365-10369, 1993. Briefly, membrane preparations were obtained from human recombinant (HEK 293) cells in which the human adenosine-$A_3$ receptor was stably expressed. Membranes were incubated at 22° C. for 90 minutes with [$^{125}$I]-AB-MECA in the absence or presence of testcompounds in a concentration range from 10 µM down to 0.1 nM, diluted in a suitable buffer. Separation of bound radioactivity from free was done by filtration through Packard GF/B glass fiber filters with several washings with ice-cold buffer using a Packard cell harvester. Bound radioactivity was measured with a scintillation counter (Topcount, Packard) using a liquid scintillation cocktail (Microscint 0, Packard). Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_i$ values were calculated by correcting the $IC_{50}$ values for radioligand concentration and its affinity for the human adenosine-$A_3$ receptor according to the Cheng-Prusoff equation:

$$pK_i = -\log(IC_{50}/(1+S/K_d))$$

in which the $IC_{50}$ is as described above, S is the concentration [$^{125}$I]-AB-MECA used in the assay expressed in mol/l (typically 0.1 nM), and $K_d$ is the equilibrium dissociation constant of [$^{125}$I]-AB-MECA for human adenosine-$A_3$ receptors (0.22 nM).

Determination of In Vitro Functional Activity on Human Adenosine $A_3$ Receptors Using an Aequorin-based Assay A stable monoclonal hA3-Aequorin cell line was provided by Euroscreen. The coding region encoding the human Adenosine A3 receptor was amplified by polymerase chain reaction (PCR), using human lung cDNA as template. The PCR product was ligated in the expression vector pEFIN3 (Invitrogen), and the complete sequence of the insert was then established. Sequencing revealed a complete identity with the sequence published by Salvatore, C. A. et al. (Acc. Number GenBank: L22607). The expression plasmid containing the coding sequence of the human Adenosine A3 receptor was transfected in CHO-K1 cells stably expressing mitochondrially targetted Aequorin and G$\alpha$16. Resistant clones were selected in the presence of 400 µg/ml G418 and isolated by limiting dilution. The clone with the best response to 2-CI-IB-MECA was selected for further work. The hA3-Aequorin cells express mitochondrially targetted apo-Aequorin. Cells have to be loaded with coelenterazine, in order to reconstitute active Aequorin. After binding of agonists to the hA3 receptor, the intracellular calcium concentration increases, which leads to a luminescent response. Binding of calcium to the apo-Aequorin/coelenterazine complex leads to an oxidation reaction of coelenterazine, which results in the production of apo-Aequorin, coelenteramide, $CO_2$ and light ($\lambda_{max}$ 469 nm). This luminescent response is dependent on the agonist concentration.

Assay-protocol:
Dilute the loaded cells 18× in Dulbecco's medium without PhenolRed (Gibco BRL), pre-heated to 37° C., resulting in a concentration of 2.8*$10^5$ cells/ml.
Stir for 1 hour at room temperature.
Add 10 µl compound or control per well in white 96-well plates.
Add 90 µl of diluted cells (2.5*$10^4$ cells/well).
Measure chemoluminescence immediately for 20 seconds.
In antagonist mode 50 µl $10^{-6}$ N6-benzyl-NECA is added as the agonist.
Measure chemoluminescence immediately for 20 seconds using the MicroBetaJet (PerkinElmer).

Adenosine receptor subtype selectivity of the compounds of the invention was determined using the methods described below In Vitro Affinity for Human Adenosine-$A_1$ Receptors Affinity of the compounds for human adenosine-$A_1$ receptors was determined using the receptor binding assay described by A. Townsend-Nicholson and P. R. Schofield (*Biol. Chem.*, 269, 2373, 1994), using human recombinant receptors expressed in CHO cells, and [$^3$H]DPCPX as radioligand.

In Vitro Affinity for Human Adenosine-$A_{2A}$ Receptors

Affinity of the compounds for human adenosine-$A_{2A}$ receptors was determined using the receptor binding assay described by D. R. Luthin et al., (*Mol. Pharmacol.*, 47, 307, 1995), using human recombinant receptors expressed in HEK-293 cells, and [$^3$H]CGS 21680 as radioligand.

In Vitro Affinity for Human Adenosine-$A_{2B}$ Receptors

Affinity of the compounds for human adenosine-$A_{2B}$ receptors was determined using the receptor binding assay described by J. H. Stehle et al. (*Mol. Endocrinol.*, 6, 384, 1992), using human recombinant receptors expressed in HEK-293 cells, and [$^3$H]MRS 1754 as radioligand.

The compounds of the invention have affinity for adenosine-$A_3$ receptors in the binding assay described above, and were shown to be antagonists in the functional assay, also described above. These properties make them useful in the treatment of disorders in which adenosine-$A_3$ receptors are involved, or that can be treated via manipulation of these receptors.

According to the procedures described above the compounds of the invention can be prepared. They are intended to further illustrate the invention in more detail, and therefore are not deemed to restrict the scope of the invention in any way.

Dose

The affinity of the compounds of the invention for adenosine $A_3$ receptors was determined as described above. From the binding affinity measured for a given compound of formula (1), one can estimate a theoretical lowest effective dose. At a concentration of the compound equal to twice the measured $K_i$-value, nearly 100% of the adenosine $A_3$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

Treatment

The term "treatment" as used herein refers to any treatment of a mammalian, preferably human, condition or disease, and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

Abbreviations

Inasmuch not explained in the text, several generally accepted abbreviations are used in the following parts:
$CF_3$TMS=trimethylsilyltrifluoromethane
DCM=dichloromethane
DMAP=4-dimethylaminopyridin
DME=1,2-dimethoxyethane
DMF=dimethylformamide
EA=ethylacetate
NaOMe=sodiummethoxide
MTBE=methyl-t-butyl ether
PE=petroleum ether

EXAMPLES

Example 1

Materials and Methods

All reactions involving moisture-sensitive compounds were carried out under a dry nitrogen atmosphere. Dichloromethane (phosphorous pentaoxide and calciumhydride), tetrahydrofuran (sodium/benzophenone ketyl) and light petroleum (60-80) were freshly distilled prior to use. All other commercially available chemicals were used without further purification. Reactions were monitored by using thin-layer chromatography (TLC) on silica coated plastic sheets (Merck silica gel 60 F254) with the indicated eluent. The compounds were visualised by UV light (254 nm) or $I_2$. Flash chromatography refers to purification using the indicated eluent and Acros silica gel (0.030-0.075 mm). Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, unless indicated otherwise. $^{19}$F NMR and $^{13}$C NMR experiments were carried out on a Varian Inova 500 spectrometer operating at 11.74 T (499.9 MHz for $^1$H; 125.7 MHz for $^{13}$C; 50.7 Mhz, 470.4 MHz for $^{19}$F) using a 5 mm SW probe. The spectra were determined in deuterated chloroform or dichloromethane obtained from Cambridge Isotope Laboratories Ltd. Chemical shifts (δ) are given in ppm downfield from tetramethylsilane (1H, 13C) or CCl3F ($^{19}$F). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of $D_2O$. Melting points were measured with a Büchi B-545 Melting Point apparatus. Mass spectra and accurate mass measurements were performed using a JEOL JMS-SX/SX 102 A Tandem Mass Spectrometer using Fast Atom Bombardement (FAB). A resolving power of 10,000 (10% valley definition) for high resolution FAB mass spectrometry was used. Extinction coefficients were determined with a HP 8453 UV-Vis spectrophotometer. Analytical HPLC was performed on a C18 column (Inertsil ODS-3, particle size 3 mm; 4.6 mm 50 mm) using the following elution gradient: linear gradient of 5% to 95% aqueous $CH_3CN$ containing 0.04% $HCO_2H$ over 5 min, then 95% aqueous $CH_3CN$ containing 0.04% $HCO_2H$ for 2 min at 2.0 ml min$^{-1}$. Products were detected at λ=254 nm.

Example 2

Syntheses of Intermediates

Intermediate A: 2-nitro-6-chloro-9-methyl purine

Trifluoroacetic acid anhydride (TFAA) (3.95 ml; 28 mmol) was added dropwise to a solution of commercially available 6-chloro-9-Me-purine (3 g; 17 mmol) and tetrabutylammoniumnitrate (TBAN) (8.65 g; 28 mmol) in dry DCM (50 ml) at 0° C. under a nitrogen atmosphere. After stirring for 1.5 h the solution was poured into 100 ml of saturated aqueous $NaHCO_3$-ice (1:1) and $Et_2O$ (100 ml) was added. The aqueous layer was extracted with 3 portions of 60 ml $Et_2O$—$CH_2Cl_2$ (3:1). The collected organic layers were washed with $H_2O$ (2×50 ml) and brine (1×50 ml) and dried with $Na_2SO_4$. Evaporation to dryness afforded the crude product (2 g). Stirring in MeOH and filtration yielded the pure product (1.66 g; 46%). $^1$H NMR (CDCl$_3$) δ 8.37 (s, 1H, H-8), 4.06 (s, 3H, Me)

Intermediate B: 6-chloro-9-Boc purine

A suspension of commercially available 6-chloropurine (15.5 g; 0.10 mol), Boc$_2$O (31 g; 0.14 mol) and DMAP (0.3 g; 2 mmol) in dry $CH_2Cl_2$ (150 ml) was stirred for 3 h until a clear solution was obtained. Light petroleum (25 ml) and silica gel (10 g) were added, the mixture was filtered over Hyflo and the solids were rinsed with EtOAc. Evaporating the solvent yielded the crude product (24.4 g; 96%). Recrystallisation from a mixture of EtOAc-light petroleum afforded a first batch of white needles (12.1 g; 48%). A second batch was obtained by recrystallising the concentrated filtrate (10.5 g; 41%). decomp.>111° C.; $^1$H NMR (CDCl$_3$) δ 8.90 (s, 1H, H-2), 8.55 (s, 1H, H-8), 1.71 (s, 9H, CCH3). 13C NMR (CDCl3) δ 153.46 (d, J 211.2, C-2), 151.06 (d, J 13.2, C-6) 150.84 (dd, J 12.6, J 4.7, C-4), 144.83 (CO), 144.26 (d, J 221.6, C-8), 132.02 (dd, J 12.7, J 1.2, C-5), 87.49 (—CCH3), 27.22 (q, J 127.6, —CCH3). H-8 was identified by a NOE-experiment (400 MHz, CDCl3): saturation (4.5 s) of the t-Bu protons led to 0.29% NOE on H-8 and 0% on H-2.

Intermediate C: 6-chloro-9-BocOM purine

To a solution of 6-chloro-9-Boc-purine (5.65 g, 22 mmol, intermediate B) in dichloromethane para-formaldehyde (1 g, 33 mmol) and DMAP (0.27 g; 2.2 mmol) were added. The mixture was refluxed for 4 h until the conversion was complete according to HPLC. Silica was added and the solvent was evaporated. Flashchromatography (EA/PE 2:3) furnished the product in 65% yield as a colourless oil. A white solid was collected by extensive evaporation in vacuo. $^1$H NMR (CDCl$_3$) δ 8.82 (s, 1H, H-8), 8.43 (s, 1H), 6.18 (s, 2H, CH$_2$—O) 1.49 (s, 9H, CCH$_3$).

Intermediate D: 6-chloro-2-nitro-9-BocOM purine

TFAA (2.25 ml; 13 mmol) was added dropwise to a solution of 6-chloro-9-BocOM-purine (2.84 g; 10 mmol, intermediate C) and TBAN (4.87 g; 13 mmol) in dry $CH_2Cl_2$ (25 ml) at 0° C. under a nitrogen atmosphere. After stirring for 1.5 h the solution was poured into 75 ml of saturated aqueous $NaHCO_3$-ice (1:1) and $Et_2O$ (75 ml) was added. The aqueous layer was extracted with 3 portions of 50 ml $Et_2O$—$CH_2Cl_2$ (3:1). The collected organic layers were washed with $H_2O$ (2×50 ml) and brine (1×50 ml) and dried with Na$_2$SO4. Evaporation to dryness afforded the crude product (2.0 g; 70%). Crystalisation from ethylacetate furnished 6-chloro-2-nitro-9-BocOM-purine as a white solid (1.85 g; 65%). $^1$H NMR (CDCl$_3$) δ 8.70 (s, 1H, H-8), 6.23 (s, 2H, CH$_2$—O) 1.50 (s, 9H, CCH$_3$). IR ν 1750

Intermediate E: 6-trifluoromethyl-2-nitro-9-BocOM purine

To a suspension of CsF (1.38 g, 9 mmol) and 6-chloro-2-nitro-9-BocOM-purine (2.0 g, 6 mmol, intermediate D) in dry THF (10 ml) CF$_3$TMS (2.7 ml, 18 mmol) was added at 0° C. After 5 minutes of stirring the ice/water bath was removed and the mixture was stirred vigorously at room temperature. After 5 h the reaction was quenched by adding silica gel. The suspension was concentrated to dryness under reduced pressure. The resulting powder was purified by column chromatography (EA/PE 1:1)) and concentrated under reduced pressure. The resulting pure product (0.8 g, 31%) was obtained as a light yellow solid. $^1$H-NMR (400 MHz, CDCl$_3$), δ [ppm]: 8.59 (s, 1H, H-8), 6.20 (s, 2H, CH$_2$O),1.48 (s, 9H). $^{19}$F-NMR (500 MHz, CDCl$_3$), δ [ppm]: −69.08 (6-CF$_3$).

Intermediate F: 6-trifluoromethyl-9-(tri-O-acetate-ribose)-2-nitro purine

To a suspension of CsF (5.3 g, 35 mmol) and 6-chloro-9-(2,3,5-tri-O-acetate-ribose)-2-nitropurine (10.0 g, 21.8 mmol) (see: Wanner, Kunzel, Ijzerman and Koomen, "2-*nitro analogues of adenosine and 1-deazaadenosine: Synthesis and binding studies at the adenosine A*(1), *A*(2*A*) *and A*(3) *receptor subtypes*". *Bioorganic & Medicinal Chemistry Letters* 2000, 10, 2141-2144) in dry THF (40 ml) CF$_3$TMS (5.2 ml, 35 mmol) was added at 0° C. After 5 minutes of stirring the ice/water bath was removed and the mixture was stirred vigorously at room temperature. The reaction was followed by HPLC (R$_{t,product}$=3.7 and R$_{t,reactant}$=3.3). After 19 h the reaction was quenched by adding silica gel. The suspension was concentrated to dryness under reduced pressure. The resulting powder was purified by column chromatography using a gradient mixture of MTBE/MeOH (MTBE with 1% MeOH—MTBE with 4% MeOH) and concentrated under reduced pressure. The resulting pure product (2.7 g, 25%) was obtained as a light yellow foam.

$^1$H-NMR (400 MHz, CDCl$_3$), δ [ppm]: 8.45 (s, 1H, H-8'), 6.27 (d, J=5.3 Hz, 1H, H-1'), 5.81 (t, J=5.5 Hz, 1H, H-2'), 5.62 (t, J=5.1 Hz, 1H, H-3'), 4.52 (m, 1H, H-4'), 4.43 (m, 2H, 5'-CH$_2$), 2.18 (s, 3H, acetyl), 2.11 (s, 3H, acetyl), 2.09 (s, 3H, acetyl). $^{19}$F-NMR (500 MHz, CDCl$_3$), δ [ppm]: −69.06 (6-CF$_3$).

G: 2-phenethylamino-6-trifluoromethyl-9-(tri-O-acetate-ribose) purine

A THF (10 ml) solution containing 6-Trifluoromethyl-9-(tri-O-acetate-ribose)-2-nitropurine (2.6 g, 5.3 mmol, intermediate F), Et$_3$N (0.97 ml, 6.9 mmol) and phenylethylamine (0.66 ml, 5.3 mmol) was stirred at 0° C. for 22 h while warming up till room temperature. The reaction was followed by HPLC. After completion the reaction was quenched by adding silica gel. The suspension was concentrated to dryness. The resulting powder was purified by column chromatography using a gradient mixture of MTBE: MTBE with 1% MeOH—MTBE with 4% MeOH and concentrated under reduced pressure. The resulting pure product was obtained as a yellow/white foam in 90% yield.

$^1$H-NMR (400 MHz, CDCl$_3$), δ [ppm]: 7.96 (s, 1H, H-8), 7.34-7.21 (m, 5H, H$_{ar}$), 6.15 (d, J=4.9 Hz, 1H, H-1'), 6.13 (br s, 1H, NH), 5.83 (t, J=5.3 Hz, 1H, H-2'), 5.71 (t, J=5.1 Hz, 1H, H-3'), 4.45 (m, 2H, 5'-CH$_2$), 4.38 (m, 1H, H-4'), 3.93 (br m, 2H, NHC$\underline{H}_2$), 3.00 (t, J=7.1 Hz, 2H, CH$_2$), 2.16 (s, 3H, acetyl), 2.10 (s, 3H, acetyl), 2.09 (s, 3H, acetyl).

Example 3

Syntheses of Specific Compounds

Compound 1: 2-nitro-6-trifluoromethyl-9-methyl purine

To a suspension of CsF (0.144 g, 0.95 mmol) and 2-NO$_2$-6-Cl-9-Me-purine (intermediate A, 0.100 g, 0.468 mmol) in dry THF (5 ml) CF$_3$TMS (1.87 mmol) was added at 0° C. After 5 minutes of stirring the ice/water bath was removed and the mixture was stirred vigorously at room temperature. After 6 h the reaction was diluted with ether and water. The waterlayer was extracted with ether 3 times. The combined organic layers were dried with a saturated NaCl solution and treated with sodiumsulphate. The solution was concentrated to dryness under reduced pressure. The resulting oil was purified by flash chromatography (eluens EA) and concentrated under reduced pressure. The resulting pure product (0.35 g, 30%) was obtained as a white foam.

$^1$H-NMR (400 MHz, CDCl$_3$), δ [ppm]: 8.27 (s, 1H, H-8), 4.01 (s, 3H, N-Me)
$^{19}$F-NMR (500 MHz, CDCl$_3$), δ [ppm]: −69.01 (6-CF$_3$).

Compound 2: 2-morpholinyl-6-trifluoromethyl-9-β-D-ribofuranosyl purine

6-Trifluoromethyl-9-(Tri-O-acetate-ribose)-2-nitropurine (intermediate F, 0.100 g, 0.2 mmol) was treated with morpholine (0.175 ml, 2 mmol) and triethylamine (0.2 ml) in 1 ml THF. After the reaction was complete, the product was purified by flash chromatography (EA) to yield compound 2 (30 mg, 37%).

$^1$H-NMR (400 MHz, DMSO), δ [ppm]: 8.6 (s, 1H, H-8), 6.00 (d, 1H, H-1'), 5.64 (d, 1H, H-2'), 5.47 (d, 1H, H-3'), 4.66 (m, 2H, 5'), 4.34-4.13 (m, 8H).

Compound 3: 2-piperidinyl-6-trifluoromethyl-9-β-D-ribofuranosyl purine

2-Piperidinyl-6-trifluoromethyl-(tri-O-acetate ribose) purine was made following the procedure for intermediate G. This product (0.038 g) was treated with 1:1 NH$_3$ solution and MeOH. Flash chromatography (MTBE +2.5% MeOH) yields compound 3 (0.030 g, 40%). $^1$H-NMR (400 MHz, CDCl3), δ [ppm]: 7.89 (s, 1H, H-8), 5.82 (d, 1H, H-1'), 5.0 (t, 1H, H-2'), 4.44 (d, 1H, H-3'), 4.32 (m, 1H, 4'), 4.1 (bs, 4H), 3.93 and 3.76 (d, 2H, H5'), 1.72 (m, 6H).

Cmp 4: 2-(4-OH-piperidinyl)-6-trifluoromethyl-9-β-D-ribofuranosyl purine 2-(4-OH-piperidinyl)-6-trifluoromethyl-(tri-O-acetate ribose) purine was made following the procedure for intermediate G. This product (0.040 g, 0.07 mmol) was treated with 1:1 NH$_3$ solution and MeOH. Flash chromatography (MTBE +2.5% MeOH) yields compound 4 (0.020 g, 65%).
$^1$H-NMR (400 MHz, DMSO, D$_2$O), δ [ppm]: 7.86 (s, 1H, H-8), 5.80 (d, 1H, H-1'), 5.2 (t, 1 H, H-2'), 4.6 (d, 1H, H-3'), 4.29 (m, 1H, 4'), 4.1 (bs, 4H), 3.80 and 3.74 (d, 2H, H5'), 1.90 (m, 4H).

C5: 2-(OH-ethyl-piperazinyl)-6-trifluoromethyl-9-β-D-ribofuranosyl purine

A THF (5 ml) solution containing 6-Trifluoromethyl-9-(2,3,5-Tri-O-acetate-ribose)-2-nitropurine (0.374 g, 0.8 mmol) and hydroxy-ethylpiperazine (1.0 ml, 8.1 mmol) was stirred at room temperature for 18 h. The reaction was followed by HPLC. After completion the reaction was quenched by adding silica gel. The suspension was concentrated to dryness. The resulting powder was purified by column chromatography using a gradient mixture of MTBE: MTBE with 1% MeOH—MTBE with 4% MeOH and concentrated under reduced pressure. The resulting pure product was obtained in 60% yield.

$^1$H-NMR (400 MHz, DMSO, D$_2$O), δ [ppm]: 8.57 (s, 1H, H-8), 5.99 (d, 1H, H-1'), 4.6 (t, 1H, H-2'), 4.4 (d, 1H, H-3'), 4.29 (m, 1H, 4'), 4.1 (d, 2H, H5'), 3.56 (t, 2H), 2.59 (m, 8H), 2.48 (t, 2H)

Compound 6: 6-trifluoromethyl-2-benzylamino purine

A solution of 6-trifluoromethyl-2-benzylamino-9-BocOM purine (compound 29, 0.100 g, 0.23 mmol) in MeONa/MeOH (2.3 mmol) was stirred at room temperature. After 45 minutes solid CO$_2$ was added. Water was added slowly to the suspension. The solid was filtered and washed with water. After drying at 50° C. in vacuo, it was collected as a pure solid (0.060 g, 89%)

$^1$H-NMR (400 MHz, DMSO-d$_6$), δ [ppm]: 13.0 (br s, 1H, 9-NH), 8.34 (br s, 1H, NH), 8.33 (s, 1H, H-8), 7.38-7.23 (m, 5H, H$_{ar}$), 4.71 (br s, 2H, NHC$\underline{H}_2$)

Compound 7: 6-trifluoromethyl-9-methyl-2-benzylamino purine

Compound 7 was made via Mitsunobu conditions with polymer bound triphenylphosphine to facilitate purification. To a solution of 6-trifluoromethyl-2-benzylaminopurine (compound 6, 0.047 g, 0.16 mmol) in DCM (2 ml), was added triphenylphosphine polymer bound (0.133 g, 3 mmol/g, 0.4 mmol), MeOH (0.016 ml, 0.4 mmol) and diisopropylazodicarboxylate (DIAD) (0.078 ml, 0.4 mmol). The mixture was stirred slowly at room temperature and after 1 h the reaction was complete. Flash chromatography (EA) afforded compound 7 (0.035 g, 71%)

$^1$H-NMR (400 MHz, CDCl$_3$), δ [ppm]: 7.80 (s, 1H, H-8), 7.34-7.22 (m, 5H, H$_{ar}$), 6.15 (br s, 1H, NH), 4.01 (s, 3H), 3.95 (br s, 2H, NHC$\underline{H}_2$)

Compound 8: 2-benzylamino-6-trifluoromethyl-9-β-D-ribofuranosyl purine 2-benzylamino-6-trifluoromethyl-9-(tri-O-acetate-ribose) purine was made according to the procedure for intermediate G. This product (0.090 g, 0.16 mmol) was stirred in a 1:1 solution of NH$_3$ in MeOH for 4 h. Solvent evaporation and sublimation afforded compound 8 (0.057 g, 82%).

$^1$H-NMR (400 MHz, DMSO), δ [ppm]: 8.55 (s, 1H, H-8), 7.37-7.23 (m, 5H, H$_{ar}$), 6.5 (br s, 1H, NH), 5.94 (d, 1H, H-1'), 5.49 (d, 1H, OH), 5.27 (bs, 1H, OH), 5.25 (bs, 1H, OH), 4.72 (t, 1H, H-2'), 4.61 (t, 1H, H-3'), 4.38 (m, 1H, H-4'), 4.13 (br m, 2H, NHC$\underline{H}_2$), 3.97 (2H, H5');

$^{19}$F-NMR (500 MHz, DMSO), δ [ppm]: −68.64 (6-CF$_3$).

Compound 9: 6-trifluoromethyl-2-phenethylamino purine

A solution of intermediate G, 2-phenethylamino-6-trifluoromethyl-9-(tri-O-acetate-ribose)-purine (2.65 g, 4.7 mmol) in trifluoroacetic acid (15 ml) was stirred at 40° C. The reaction progress was followed by HPLC (R$_{t,product}$=3.7). After 24 h the mixture was coevaporated with toluene and methanol. Trituration with ether furnished the product as a light grey solid (1.15 g, 80%). $^1$H-NMR (400 MHz, DMSO-d$_6$), δ [ppm]: 13.4 (br s, 1H, 9-NH), 8.32 (s, 1H, H-8), 8.32 (br s, 1H, NH), 7.31-7.21 (m, 5H, H$_{ar}$), 4.16 & 3.72 (br m, 2H, NHC$\underline{H}_2$), 2.96 (t, J=7.5 Hz, 2H, CH$_2$).

Compound 10: 6-trifluoromethyl-methyl-2-phenethylamino purine

To a solution of 6-Trifluoromethyl-2-phenethylaminopurine (compound 9, 0.600 g, 1.95 mmol) in DMF (14 ml) K$_2$CO$_3$ (0.351 g, 2.54 mmol) and MeI (0.158 ml, 2.54 mmol) were added. The mixture was stirred at room temperature and after 0.5 h the reaction was complete (HPLC: R$_{t,product}$=4.1). Crystallization occurred after the slow addition of water (17 ml). After stirring for 0.5 h the mixture was filtrated and the residue was washed with four 10-ml portions of water. The filtrate was again filtrated after 1 h and the residue was washed with three 5-ml portions of water. The residue was dried in vacuo at 60° C. obtaining the product as a white solid (503 mg, 80%).

$^1$H-NMR (400 MHz, CDCl$_3$), δ [ppm]: 7.83 (s, 1H, H-8), 7.33-7.21 (m, 5H, H$_{ar}$), 6.17 (br s, 1H, NH), 3.95 (br m, 2H, NHC$\underline{H}_2$), 3.87 (s, 3H, CH$_3$), 3.01 (t, J=7.1 Hz, 2H, CH$_2$)

Compound 11: 8-bromo-6-trifluoromethyl-9-methyl-2-phenethylamino purine

6-Trifluoromethyl-9-methyl-2-phenethylaminopurine (compound 10, 100 mg, 0.312 mmol) was dried in vacuo at 100° C. for 2.5 h. After cooling, dry THF (4 ml) was added at room temperature and the solution was cooled to −72° C. (ethanol/dry ice). After addition of n-BuLi (0.49 ml of a 1.6 M solution in hexane, 0.779 mmol) the colourless solution turned yellow. After 15 minutes Br$_2$ (26 μL, 0.498 mmol) was added and after 5 minutes the reaction was complete (HPLC: R$_{t,product}$=4.6). To the red solution silica gel (~4 g) was added and the suspension was evaporated to dryness. Flashchromatography (2% MeOH in MTBE) and freeze drying afforded compound 11 (110 mg, 88%) as a white fluffy solid, mp 131-139° C.

$^1$H-NMR (400 MHz, CDCl$_3$), δ [ppm]: 7.33-7.21 (m, 5H, H$_{ar}$), 5.91 (br s, 1H, NH), 3.93 (br m, 2H, NHC$\underline{H}_2$), 3.80 (s, 3H, CH$_3$), 2.98 (t, J=7.1 Hz, 2H, CH$_2$). $^{19}$F-NMR (500 MHz, CDCl$_3$), δ [ppm]: −70.18 (6-CF$_3$).

Compound 12: 8-iodo-6-trifluoromethyl-9-methyl-2-phenethylamino purine

6-Trifluoromethyl-9-methyl-2-phenethylaminopurine (compound 10) (0.500 g, 1.56 mmol) was dried in vacuo at 100° C. for 2.5 h. After cooling, dry THF (18 ml) was added at room temperature and the solution was cooled to −72° C. (ethanol/dry ice). After addition of n-BuLi (2.4 ml of a 1.6 M solution in hexane, 3.9 mmol) the colourless solution turned yellow. After 15 minutes I$_2$ (0.633 g, 2.49 mmol) was added and after 5 minutes the reaction was complete (HPLC: R$_{t,product}$=4.7). To the red solution silica gel (~4 g) was added and the suspension was evaporated to dryness. Flash chromatography (1% MeOH in MTBE) and freezedrying afforded the product (0.637 g, 91%) as fluffy white crystals, mp 139-142° C. $^1$H-NMR (400 MHz, CDCl$_3$), δ [ppm]: 7.33-7.21 (m, 5H, H$_{ar}$), 5.96 (br s, 1H, NH), 3.93 (br m, 2H, NHC$\underline{H}_2$), 3.77 (s, 3H, CH$_3$), 2.98 (t, J=7.1 Hz, 2H, CH$_2$). $^{19}$F-NMR (500 MHz, CDCl$_3$), δ [ppm]: −70.12 (6-CF$_3$).

Cp 13: 8-(furan-2-yl)-6-trifluoromethyl-9-methyl-2-phenethylamino purine

This compound was prepared from compound 12 (20 mg, 0.045 mmol), 2-furanboronic acid (25 mg, 0.224 mmol), Pd(PPh$_3$)$_4$ (13 μg, 0.011 mmol) and Na$_2$CO$_3$ (aq, 0.447 mmol) in DME/H$_2$O (8:1) (4.5 ml) by the procedure described for the preparation of compound 19. After completion (HPLC: R$_{t,product}$=4.8; TLC (EA/PE 1:3): R$_{f,product}$=0.09) the workup of the reaction mixture followed. Silica gel column chromatography (PE/EA (2:1), 120 ml) gave compound 13 (15 mg, 87%) after evaporation as a white solid. $^1$H-NMR (500 MHz, CDCl$_3$), δ [ppm]: 7.68 (s, 1H), 7.35-7.25 (m, 5H, H$_{ar}$), 7.16 (s, 1H), 6.65 (s, 1H), 6.12 (br s, 1H, NH), 4.08 (s, 3H, CH$_3$), 3.98 (br m, 2H, NHC$\underline{H}_2$), 3.03 (t, J=7.0 Hz, 2H, CH$_2$). $^{19}$F-NMR (500 MHz, CDCl$_3$), δ [ppm]: −69.96 (6-CF$_3$). $^{13}$C-NMR (500 MHz, CDCl$_3$) δ [ppm]: 154.19, 150.64 (q, J=38 Hz), 150.12, 144.75, 144.2, 143.13, 138.67, 128.83 (2C), 128.59 (2C), 126.50, 120.05 (q, J=275 Hz, CF$_3$), 119.72, 113.06, 112.16, 42.15 35.73, 30.81. MS: m/z 388.1381 (M$^+$+H. C$_{19}$H$_{17}$ON$_5$F$_3$ requires 388.1385).

Cmp 14: 8-(thien-2-yl)-6-trifluoromethyl-9-methyl-2-phenethylamino purine

This compound was prepared from compound 12 (20 mg, 0.045 mmol), 2-thiopheneboronic acid (12 mg, 0.089 mmol), Pd(PPh$_3$)$_4$ (13 mg, 0.011 mmol) and Na$_2$CO$_3$ (51 mg, 0.179 mmol) in DME/H$_2$O (6:1) (2.0 mL) by the procedure described for the preparation of 19 to give compound 14 (11 mg, 55%) as a yellow solid. $^1$H-NMR (400 MHz, CDCl$_3$), δ [ppm]: 7.62 (d, 1H), 7.55 (d, J=0.7 Hz, 1H), 7.31-7.20 (m, 5H$_{ar}$), 6.13 (br s, 1H, NH), 4.02 (s, 3H, CH$_3$), 3.94 (br m, 2H, NHC$\underline{H}_2$), 3.02 (t, J=7.3 Hz, 2H, CH$_2$).

C15: 8-N-pyrrolidinyl-6-trifluoromethyl-9-methyl-2-phenethylamino purine

Compound 12 (10 mg, 0.022 mmol) was dissolved in pyrrolidine (2 ml, 24 mmol) and stirred at 90° C. under dry N$_2$. The progress of the reaction was followed with HPLC ($R_{t,product}$=4.3) and TLC ($R_{f,product}$=0.55 in MTBE with 2% MeOH). After 17 hours the solution was diluted with DCM (4 ml) and evaporated with silica gel to dryness. Flash chromatography (Ø=1.2 cm, EA/PE 1:2, gradient EA) gave, after evaporation, compound 15 (4.8 mg, 56%) as a white solid. $^1$H-NMR (400 MHz, CDCl$_3$), δ [ppm]: 7.32-7.19 (m, 5H, H$_{ar}$), ~5.6 (br s, 1H, NH), 3.90 (q, J=6.9 Hz, 2H, NHCH$_2$), 3.77 (s, 3H, CH$_3$), 3.69 (br m, 4H), 2.99 (t, J=7.4 Hz, 2H, CH$_2$), 2.04 (br m, 4H).

C16: 8-N-piperidinyl-6-trifluoromethyl-9-methyl-2-phenethyl amino purine

Compound 12 (10 mg, 0.022 mmol) was dissolved in piperidine (2 ml, 24 mmol) and stirred at 90° C. under dry N$_2$. The progress of the reaction was followed by HPLC ($R_{t,product}$=5.1). After 17 hours the solution was diluted with DCM (4 ml) and evaporated with silica gel to dryness. Silica gel column chromatography (Ø=1.2 cm, EA/PE 1:1) gave, after evaporation, compound 16 (9 mg, 99%) as a white-yellow solid. $^1$H-NMR (400 MHz, CDCl$_3$), δ [ppm]: 7.33-7.20 (m, 5H, H$_{ar}$), ~5.8 (br s, 1H, NH), 3.92 (q, J=6.2 Hz, 2H, NHCH$_2$), 3.64 (s, 3H, CH$_3$), 3.26 (br m, 4H), 2.99 (t, J=7.4 Hz, 2H, CH$_2$), 1.79-1.73 (br m, 4H), 1.69-1.67 (br m, 2H).

C17: 8-N-morpholinyl-6-trifluoromethyl-9-methyl-2-phenethylamino purine

This compound was prepared from compound 12 (10 mg, 0.022 mmol) and morpholine (2 mL, 23 mmol) by the procedure described for the preparation of compound 16. HPLC: $R_{f,product}$=4.4 and TLC: $R_{f,product}$=0.49 (MTBE with 2% MeOH). Flash chromatography (Ø=1.2 cm, EA/PE 2:1) gave, after evaporation, compound 17 (8.3 mg, 90%) as a orange solid. $^1$H-NMR (400 MHz, CDCl$_3$), δ [ppm]: 7.33-7.21 (m, 5H, H$_{ar}$), ~5.8 (br s, 1H, NH), 3.94 (br m, 2H, NHCH$_2$), 3.88 (t, J=4.7 Hz, 4H, H-11 and H-15), 3.67 (s, 3H, CH$_3$), 3.30 (t, J=4.7 Hz, 4H), 2.99 (t, J=7.3 Hz, 2H, CH$_2$).

Compound 18: 8-cyclopentylamino-6-trifluoromethyl-9-methyl-2-phenethylamino purine Compound 12 (10 mg, 0.022 mmol) was dissolved in cyclopentylamine (2 ml, 24 mmol) and stirred at 90° C. under dry N$_2$. HPLC: $R_{t,product}$=4.5 and TLC: $R_{f,product}$=0.29 (EA/PE 1:2). After 42 hours the reaction mixture was purified with flash chromatography (Ø=1.2 cm, EA/PE 1:2) and SPE (Supelco, packed with 1 g silica gel) (eluent: DCM with 2% MeOH, 15 ml) to afford compound 18 (6.7 mg, 75%) as a red solid. $^1$H-NMR (400 MHz, CDCl$_3$), δ [ppm]: 7.32-7.20 (m, 5H, H$_{ar}$), ~5.7 (br s, 1H, NH), 4.30-4.25 (m, 1H), ~4.2 (br s, 1H), 3.91 (m, 2H, NHCH$_2$), 3.53 (s, 3H, CH$_3$), 2.99 (t, J=7.4 Hz, 2H, CH$_2$), 2.16-2.12 (m, 2H, cyclopentyl), 1.79-1.65 (m, 4H, cyclopentyl), 1.57-1.54 (m, 2H, cyclopentyl).

Cmp 19: 8-phenyl-6-trifluoromethyl-9-methyl-2-phenethylamino purine

8-Iodo-6-trifluoromethyl-9-methyl-2-phenethylaminopurine (compound 12, 40 mg, 0.089 mmol), Pd(PPh$_3$)$_4$ (26 mg, 0.022 mmol) and phenylboronic acid (22 mg, 0.179 mmol) were dissolved in DME (4 ml) and after addition of Na$_2$CO$_3$·10H$_2$O (102 mg, 0.358 mmol) in H$_2$O (0.5 ml) the solution was stirred at 90° C. under Ar. The progress of the reaction was followed by HPLC ($R_{t,product}$=5.0). After 17 hours the mixture was diluted with EA (10 ml) and water (5 ml). The water layer was extracted two times with EA (7 ml). The organic layers were washed with water (10 ml) and a saturated NaCl solution in water (10 ml). The organic layer was dried with Na$_2$SO$_4$. Flash chromatography (Ø=1.2 cm, EA/PE 1:3) afforded compound 19 (33 mg, 93%) as a light brown solid. UV (EA) λ$_{max}$=304 nm (ε=1.5×10$^4$). $^1$H-NMR (400 MHz, CDCl$_3$), δ [ppm]: 7.75 (d, J=3.1 Hz, 2H), 7.56-7.53 (m, 3H), 7.32-7.22 (m, 5H, H$_{ar}$), 6.12 (br s, 1H, NH), 3.93 (br m, 2H, NHCH$_2$), 3.92 (s, 3H, CH$_3$), 3.01 (t, J=7.2 Hz, 2H, CH$_2$). MS: m/z 398.1601 (M$^+$+H. C$_{21}$H$_{19}$N$_5$F$_3$ requires 398.1593).

Compound 20: 8-(3-fluorophenyl)-6-trifluoromethyl-9-methyl-2-phenethylamino purine This compound was prepared from compound 12 (40 mg, 0.089 mmol) and 3-fluorophenylboronic acid (25 mg, 0.179 mmol) by the procedure described for the preparation of compound 19. The reaction was monitored by TLC and HPLC (HPLC: $R_{t,product}$=5.0; TLC (EA/PE 1:3): $R_{f,product}$=0.22, $R_{f,reactant}$=0.15). After the conversion was complete, the mixture was diluted with EA (10 ml) and water (5 ml). The water layer was extracted two times with EA (7 ml). The organic layers were washed with water (10 ml) and a saturated NaCl solution in water (10 ml). The organic layer was dried with Na$_2$SO$_4$. Flash chromatography (gradient: PE/EA (4:1)—PE/EA (2:1), 120 mL) afforded, after evaporation, compound 20 (33 mg, 88%) as a white solid.

UV (EA) λ$_{max}$=308 nm (ε=1.7×10$^4$).

$^1$H-NMR (400 MHz, CDCl$_3$), δ [ppm]: 7.54-7.48 (m, 3H, F-phenyl), 7.33-7.22 (m, 6H, 5H$_{ar}$+1H F-phenyl), 6.07 (br s, 1H, NH), 3.94 (br m, 2H, NHCH$_2$), 3.93 (s, 3H, CH$_3$), 3.02 (t, J=7.2 Hz, 2H, CH$_2$).

$^{19}$F-NMR (500 MHz, CDCl$_3$), δ [ppm]: −69.97 (3F, 6-CF$_3$), −111.36 (1F, 18-F).

$^{13}$C-NMR (500 MHz, CDCl$_3$) δ [ppm]: 162.81 (d, J=248 Hz), 154.52, 150.73 (2), 138.66, 131.15, 130.74 (d, J=8 Hz), 128.85 (2), 128.63 (2), 126.54, 124.60 (d, J=3 Hz), 120.05 (q, J=275 Hz), 119.86, 117.52 (d, J=21 Hz), 116.15 (d, J=23 Hz), 42.15, 35.72, 31.05

MS: m/z 416.1489 (M$^+$+H. C$_{21}$H$_{18}$N$_5$F$_4$ requires 416.1498).

Cmp 21: 8-E-styryl-6-trifluoromethyl-9-methyl-2-phenethylamino purine

This compound was prepared from compound 12 (40 mg, 0.089 mmol) and E-2-phenylvinylboronic acid (26 mg, 0.179 mmol) by the procedure described for the preparation of compound 19. The reaction was monitored by HPLC ($R_{t,product}$=5.2) and TLC (EA/PE 1:3) ($R_{f,product}$=0.24). Workup of the reaction mixture and flash chromatography (gradient: EA/PE (1:5)—EA/PE (1:2), 150 mL) gave, after evaporation, compound 21 (38 mg, 100%) as a red/orange oil. Yellow crystals (24 mg) were obtained after crystallization from methanol. $^1$H-NMR (400 MHz, CDCl$_3$), δ [ppm]: 7.85 (d, J=15.9 Hz, 1H), 7.60 (d, J=7.0 Hz, 2H), 7.44-7.37 (m, 3H), 7.34-7.24 (m, 5H, H$_{ar}$), 7.05 (d, J=15.9 Hz, 1H), 6.08 (br s, 1H, NH), 3.97 (br m, 2H, NHCH$_2$), 3.90 (s, 3H, CH$_3$), 3.03 (t, J=7.2 Hz, 2H, CH$_2$).

$^{13}$C-NMR (500 MHz, CDCl$_3$) δ [ppm]: 153.32, 151, 149.41, 140, 138.69 134.96, 130.12, 129.03 (2C), 128.90 (2C), 128.61 (2C), 127.68 (2C), 126.52, 119.95 (q, J=275 Hz), 118.2, 110.70, 42.39, 35.69, 29.16.

MS: m/z 424.1742 (M$^+$+H. C$_{23}$H$_{21}$N$_5$F$_3$ requires 424.1749).

Cmp 22: 8-Z-styryl-6-trifluoromethyl-9-methyl-2-phenethylamino purine

Compound 21 was converted into 8-Z-styryl-6-trifluoromethyl-9-methyl-2-phenethyl-aminopurine by exposure to daylight for 1-2 h in dichloromethane.

$^1$H-NMR (400 MHz, CDCl$_3$), δ [ppm]: characteristic doublet from 7.05 (d, E-form, J=15.9 Hz, H-11) to 6.53 (d, Z-form, J=12.3 Hz, 1H).

Compound 23: 8-phenylacetylene-6-trifluoromethyl-9-methyl-2-phenethylamino purine Compound 12 (60 mg, 0.134 mmol), Pd(PPh$_3$)$_4$ (15 mg, 0.013 mmol), Cu (I) (6 mg, 0.033 mmol) and phenylacetylene (0.026 ml, 0.234 mmol) were stirred in dry DMF (2 ml). Et$_3$N (0.023 ml, 0.168 mmol) was added and the mixture was stirred under Ar. After 2 hours the reaction mixture was diluted with ether (10 ml) and water (10 ml). The water layer was extracted three times with ether (10 ml). The organic layers were washed with water (10 ml) and a saturated NaCl solution in water (10 ml). The organic layer was dried with Na$_2$SO$_4$. Flash chromatography (Ø=1.2 cm, EA/PE 1:3) afforded compound 23 (54 mg, 96%) as a solid. $^1$H-NMR (400 MHz, CDCl$_3$), δ [ppm]: 7.65 (d, 2H), 7.47-7.40 (m, 3H), 7.33-7.22 (m, 5H, H$_{ar}$), 6.12 (br s, 1H, NH), 3.94 (br m, 2H, NHC$\underline{H}_2$), 3.92 (s, 3H, CH$_3$), 3.01 (t, 2H, CH$_2$). MS: m/z 422.1581 (M$^+$+H. C$_{23}$H$_{18}$N$_5$F$_3$ requires 422.1514).

Compound 24: 8-E-(4-trifluoromethylstyryl)-6-trifluoromethyl-9-methyl-2-phenethylamino purine This compound was prepared from compound 12 (40 mg, 0.089 mmol) and E-2-(4-trifluoromethylphenyl)vinylboronic acid (39 mg, 0.179 mmol) by the procedure described for the preparation of compound 19. The reaction was monitored by HPLC (R$_{t,product}$=5.4) and TLC (EA/PE 1:3) (R$_{f,product}$=0.22). After workup of the reaction mixture, flash chromatography (gradient: EA/PE (1:5)—EA/PE (1:2), 150 mL) furnished, after evaporation, compound 24 (44 mg, 100%) as a red/orange oil. Yellow crystals (29 mg) were obtained after crystallization from methanol. UV (EA) λ$_{max}$=354 nm (ε=2.1×10$^4$). $^1$H-NMR (400 MHz, CDCl$_3$), δ [ppm]: 7.87 (d, J=16.0 Hz, 1H), 7.71-7.66 (m, 4H), 7.35-7.23 (m, 5H, H$_{ar}$), 7.14 (d, J=15.9 Hz, 1H, H-11), 6.1 (br s, 1H, NH), 3.96 (br m, 2H, NHC$\underline{H}_2$), 3.92 (s, 3H, CH$_3$), 3.04 (t, J=7.2 Hz, 2H, CH$_2$).

$^{19}$F-NMR (500 MHz, CDCl$_3$), δ [ppm]: −63.20 (15-CF$_3$), −70.16 (6-CF$_3$).

$^{13}$C-NMR (500 MHz, CDCl$_3$) δ [ppm]: 154.03, 150.11, 149.21, 141.43, 138.68, 136.15, 131.12 (q, J=32 Hz, C-21), 128.87 (2C), 128.64 (2C), 127.54 (2C), 126.55, 125.95 (q, J=3.7 Hz, 2C), 123.89 (q, J=272 Hz), 120.05 (q, J=275 Hz), 120.1, 114.54, 42.11, 35.74, 29.04.

MS: m/z 492.1627 (M$^+$+H. C$_{24}$H$_{20}$N$_5$F$_6$ requires 492.1623).

Compound 25: 8-Z-(4-trifluoromethylstyryl)-6-trifluoromethyl-9-methyl-2-phenethylamino purine Compound 24 was completely converted into 8-Z-(4-trifluoromethylstyryl)-6-trifluoromethyl-9-methyl-2-phenethylaminopurine by exposure to daylight for 6-8 h in dichloromethane. $^1$H-NMR (400 MHz, CDCl$_3$), δ [ppm]: characteristic doublet from 7.14 (E-form, J=15.9 Hz, H-11) to 6.65 (d, Z-form, J=12.4 Hz, 1H).

Compound 26: 2-phenethylamino-6-CF$_3$-9-β-D-ribofuranosyl purine

Intermediate G, 2-phenethylamino-6-CF$_3$-9-(tri-O-acetate ribose)-purine was stirred in a 1:1 solution of NH$_3$ in methanol for 18 h. The product was purified by flashchromatography (MTBE+5% MeOH) to yield, after sublimation, compound 26 (0.033 g, 60%)

$^1$H-NMR (400 MHz, DMSO, D$_2$O), δ [ppm]: 7.99 (s, 1H, H-8), 7.34-7.21 (m, 5H, H$_{ar}$), 6.12 (br s, 1H, NH), 5.93 (bs, 1H, H-1'), 4.64 (m, 1H, H-2'), 4.27(m, 1H, H-3'), 4.19 (m, 1H, H-4'), 4.16 (m, 2H, 5'), 3.27 (br m, 2H, NHC$\underline{H}_2$), 2.7 (br m, 2H, CH$_2$).

$^{19}$F-NMR (500 MHz, DMSO), δ [ppm]: −63.95 (6-CF$_3$).

Compound 27: 2-(4-hydroxy-phenethylamino)-6-trifluoromethyl-9-β-D-ribo-furanosyl purine 2-nitro-6-CF$_3$-9-(tri-O-acetate)-purine (0.125 g, 0.25 mmol, intermediate F) was treated with 5 equivalents of tyramine in 5 ml THF. The product was purified by flashchromatography (EA) to yield compound 27 (0.046 g, 40%).

$^1$H-NMR (400 MHz, DMSO, D$_2$O), δ [ppm]: 8.52 (s, 1H, H-8), 7.39-7.0 (m, 5H, H$_{ar}$), 5.92 (bs, 1H, H-1'), 4.59 (m, 1H, H-2'), 4.16 (m, 1H, H-3'), 3.93 (m, 1H, H-4'), 3.43 (br m, 2H, NHC$\underline{H}_2$), 2.81 (br m, 2H, CH$_2$).

Compound 28: 6-trifluoromethyl-2-phenetylamino-9-BocOM-purine

A DCM (5 ml) solution containing 6-CF$_3$-2-nitro-9-BocOM-purine (0.365 mmol, intermediate E), diisopropylethylamine (0.4 mmol) and phenyl-ethylamine (0.4 mmol) was stirred at reflux temperature for 4 h. After completion the reaction was purified by flashchromatography (EA/PE 1:1). The resulting solid was triturated with PE to give compound 28 in 80% yield (0.129 g).

$^1$H-NMR (400 MHz, CDCl$_3$), δ [ppm]: 8.10 (s, 1H, H-8), 7.31-7.19 (m, 5H, H$_{ar}$), 6.23 (bs, 1H, NH), 6.09 (s, 2H, CH$_2$O), 3.92 (bs, 2H, CH$_2$NH), 2.99 (t, 2H), 1.48 (s, 9H)

Compound 29: 6-trifluoromethyl-2-benzylamino-9-BocOM-purine

A THF (5 ml) solution containing 6-Trifluoromethyl-2-nitro-9-BocOM-purine (0.4 g, 9 mmol, intermediate E), diisopropylethylamine (0.174 ml, 10 mmol) and benzylamine (0.66 ml, 10 mmol) was stirred at room temperature for 5 h. The reaction was followed with HPLC. After completion the reaction was quenched by adding silica gel. The suspension was concentrated to dryness. The resulting powder was purified by flashchromatography (EA/PE 1:1) and concentrated under reduced pressure. The resulting product was obtained in 81% yield (0.37 g).

$^1$H-NMR (400 MHz, CDCl$_3$), δ [ppm]: 8.12 (s, 1H, H-8), 7.40-7.28 (m, 5H, H$_{ar}$), 6.30 (bs, 1H, NH), 6.10 (s, 2H, CH$_2$O), 4.86 (bs, 2H, CH$_2$NH), 1.47 (s, 9H)

Cmp 30: 2-phenethyloxy-6-trifluoromethyl-9-β-D-ribofuranosyl purine

Intermediate 6-Trifluoromethyl-9-(tri-O-acetate-ribose)-2-nitropurine (0.150 g, 0.4 mmol) was dissolved in phenethylalcohol (3 ml) and K$_2$CO$_3$ (0.084 g, 0.8 mmol) was added. The reaction was warmed to 40° C. for 18 h. After cooling to room temperature, the mixture was extracted three times with DCM/water. The organic layers were concentrated and purified by flash chromatography (gradient MTBE–MTBE+10% MeOH) to give compound 30 (0.068 g, 40%).

$^1$H-NMR (400 MHz, CDCl$_3$, D$_2$O), δ [ppm]: 8.13 (s, 1H, H-8), 7.32-7.19 (m, 5H, H$_{ar}$), 5.92 (bs, 1H, H-1'), 5.0 (bs, 1H, H-2'), 4.51 (m, 1H, H-3'), 4.32 (br m, 2H, NHC$\underline{H}_2$), 3.96 (m, 1H, H-4'), 3.88 (m, 2H, 5'), 3.19 (br m, 2H, CH$_2$).

TABLE I

Structural variations of compounds 1-30

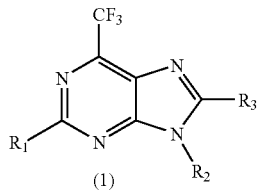

(1)

| Cp | R$_1$ | R$_2$ | R$_3$ |
|---|---|---|---|
| 1 | O$_2$N— | CH$_3$ | H |
| 2 | Morpholin-4-yl- | ribose | H |
| 3 | Piperidin-1-yl- | ribose | H |
| 4 | 4-OH-piperidinyl-1 | ribose | H |
| 5 | 4-(2-OH-ethyl)-piperazin-1-yl | ribose | H |
| 6 | Ph-CH$_2$—NH— | H | H |
| 7 | Ph-CH$_2$—NH— | CH$_3$ | H |
| 8 | Ph-CH$_2$—NH— | ribose | H |
| 9 | Ph-CH$_2$—CH$_2$—NH— | H | H |
| 10 | Ph-CH$_2$—CH$_2$—NH— | CH$_3$ | H |
| 11 | Ph-CH$_2$—CH$_2$—NH— | CH$_3$ | Br |
| 12 | Ph-CH$_2$—CH$_2$—NH— | CH$_3$ | I |
| 13 | Ph-CH$_2$—CH$_2$—NH— | CH$_3$ | furan-2-yl |
| 14 | Ph-CH$_2$—CH$_2$—NH— | CH$_3$ | thien-2-yl |
| 15 | Ph-CH$_2$—CH$_2$—NH— | CH$_3$ | Pyrrolidin-1-yl |
| 16 | Ph-CH$_2$—CH$_2$—NH— | CH$_3$ | Piperidin-1-yl |
| 17 | Ph-CH$_2$—CH$_2$—NH— | CH$_3$ | Morpholin-4-yl- |
| 18 | Ph-CH$_2$—CH$_2$—NH— | CH$_3$ | NH-cyclopentyl |
| 19 | Ph-CH$_2$—CH$_2$—NH— | CH$_3$ | phenyl |
| 20 | Ph-CH$_2$—CH$_2$—NH— | CH$_3$ | 3-F-phenyl |
| 21 | Ph-CH$_2$—CH$_2$—NH— | CH$_3$ | Ph-CH=CH— (E) |
| 22 | Ph-CH$_2$—CH$_2$—NH— | CH$_3$ | Ph-CH=CH— (Z) |
| 23 | Ph-CH$_2$—CH$_2$—NH— | CH$_3$ | Ph-C≡C— |
| 24 | Ph-CH$_2$—CH$_2$—NH— | CH$_3$ | 4-CF$_3$-Ph-CH=CH— (E) |
| 25 | Ph-CH$_2$—CH$_2$—NH— | CH$_3$ | 4-CF$_3$-Ph-CH=CH— (Z) |
| 26 | Ph-CH$_2$—CH$_2$—NH— | ribose | H |
| 27 | 4-OH-Ph-CH$_2$—CH$_2$—NH— | ribose | H |
| 28 | Ph-CH$_2$—CH$_2$—NH— | CH$_2$—O—CO—O-t-butyl | H |
| 29 | Ph-CH$_2$—NH— | CH$_2$—O—CO—O-t-butyl | H |
| 30 | Ph-CH$_2$—CH$_2$—O— | ribose | H |

Example 4

Formulations of Comp. 9 Used in Animal Studies

For oral (p.o.) administration: to the desired quantity (0.5-5 mg) of the solid Compound 9 in a glass tube, some glass beads were added and the solid was milled by vortexing for 2 minutes. After addition of 1 ml of a solution of 1% Methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid Compound 9 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 5

Pharmacological Testresults

Adenosine receptor affinity data, as well as functional adenosine-A$_3$ receptor data, obtained according to the protocols given above, are shown in the table below. All of the tested compounds have an affinity for adenosine A$_3$ receptors higher than that for the other adenosine receptor subpopulations. In all of the compounds investigated the affinity for adenosine A$_3$ receptors was shown to translate into adenosine A$_3$ receptor antagonism (pA$_2$ values ranging from 5.1-9.8). None of the investigated compounds showed adenosine A$_3$ receptor agonism in concentrations up to $10^{-5}$ M (pEC$_{50}$<5.0).

TABLE II

In vitro adenosine receptor pharmacology of compounds 1-30

| | In vitro adenosine receptor pharmacology | | | | | |
|---|---|---|---|---|---|---|
| | Adenosine receptor affinity (binding) | | | | Functional activity | |
| | | | | A3 | | |
| Comp | A$_1$ pK$_i$ | A$_{2A}$ pK$_i$ | A$_{2B}$ pK$_i$ | pK$_i$ | agonism pEC$_{50}$ | antagonism pA$_2$ |
| 1 | <5.0 | <5.0 | —.— | 5.4 | —.— | —.— |
| 3 | <5.0 | <5.0 | —.— | 5.4 | —.— | —.— |
| 4 | <5.0 | <5.0 | —.— | 4.8 | <5.0 | 6.7 |
| 6 | 5.4 | 4.7 | <5.0 | 7.7 | <5.0 | 6.8 |
| 7 | <5.0 | <5.0 | <5.0 | 5.5 | <5.0 | 5.8 |
| 8 | 5.1 | 4.9 | <5.0 | 6.5 | —.— | 7.4 |

TABLE II-continued

In vitro adenosine receptor pharmacology of compounds 1-30

| | Adenosine receptor affinity (binding) | | | Functional activity A3 | | |
|---|---|---|---|---|---|---|
| Comp | $A_1$ $pK_i$ | $A_{2A}$ $pK_i$ | $A_{2B}$ $pK_i$ | $pK_i$ | agonism $pEC_{50}$ | antagonism $pA_2$ |
| 9 | 6.0 | 4.9 | <5.0 | 7.9 | <5.0 | 8.7 |
| 10 | 5.2 | 4.8 | 4.9 | 5.8 | <5.0 | 5.5 |
| 11 | <5.0 | <5.0 | —.— | 6.0 | —.— | —.— |
| 12 | <5.0 | <5.0 | —.— | 5.6 | <5.0 | 5.7 |
| 13 | <5.0 | 5.1 | —.— | 5.9 | <5.0 | 6.8 |
| 14 | 5.2 | <5.0 | —.— | 5.8 | <5.0 | 5.8 |
| 15 | <5.0 | <5.0 | —.— | 5.5 | —.— | —.— |
| 16 | <5.0 | 4.8 | —.— | 5.4 | —.— | —.— |
| 17 | <5.0 | <5.0 | —.— | 5.8 | —.— | —.— |
| 18 | 5.5 | 5.9 | —.— | 6.2 | —.— | —.— |
| 19 | <5.0 | 5.1 | —.— | 5.7 | —.— | —.— |
| 20 | 5.1 | <5.0 | —.— | 6.0 | —.— | —.— |
| 21 | <5.0 | <5.0 | —.— | 5.4 | —.— | —.— |
| 22 | <5.0 | <5.0 | —.— | 5.7 | <5.0 | 6.0 |
| 23 | <5.0 | <5.0 | —.— | 6.3 | —.— | —.— |
| 24 | <5.0 | <5.0 | —.— | 5.4 | —.— | —.— |
| 25 | <5.0 | <5.0 | —.— | 5.3 | —.— | —.— |
| 26 | <5.0 | <5.0 | <5.0 | 7.5 | <5.0 | 9.8 |
| 27 | 5.3 | 5.5 | —.— | 8.0 | —.— | —.— |
| 28 | 5.6 | <5.0 | —.— | 7.6 | —.— | —.— |
| 29 | 5.6 | 4.7 | —.— | 7.1 | <5.0 | 5.1 |
| 30 | 5.8 | 5.5 | —.— | 6.8 | —.— | —.— |

The invention claimed is:

1. A compound of formula (1):

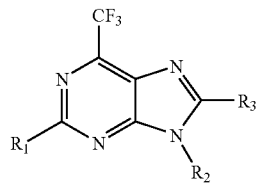

(1)

or a pharmaceutically acceptable salt, a tautomer, a stereoisomer, or a mixture of any of the foregoing wherein:

$R_1$ is chosen from —[X—$(CH_2)_n]_m$—Y, wherein X is chosen from NH and oxygen, n is chosen from 0, 1, 2 and 3, m is chosen from 0 and 1, and Y is chosen from an optionally substituted 5- or 6-membered aromatic or non-aromatic ring comprising 0, 1 or 2 hetero-atoms chosen from N, O and S; and a nitro group;

$R_2$ is chosen from hydrogen, $C_{1-3}$-alkyl, ribose, —$CH_2$—O—CO—O-t-butyl, and aryl-($C_{1-3}$)alkyl; and $R_3$ is chosen from hydrogen; halogen; $NH_2$; —NH—($C_{1-6}$)alkyl; —N-di($C_{1-6}$)alkyl; —NH-cyclo($C_{3-8}$)alkyl; $C_{2-4}$-alkenyl(hetero)aryl and $C_{2-4}$-alkynyl(hetero)aryl, wherein the hetero-atoms are chosen from N, O, and S and optionally, wherein the (hetero)aryl groups are substituted; and an optionally substituted 5- or 6-membered aromatic and non-aromatic ring, comprising 0, 1 or 2 hetero-atoms chosen from nitrogen, oxygen and sulfur.

2. The compound according to claim 1, wherein
$R_1$ is chosen from —[X—$CH_2)_n]_m$—Y, wherein X is chosen from NH and oxygen, n is chosen from 1 and 2, m is chosen from 0 and 1, and Y is chosen from an optionally substituted 6-membered aromatic and non-aromatic ring comprising 0, 1 or 2 hetero-atoms chosen from N and O, or R; and a nitro group;

$R_2$ is chosen from hydrogen, methyl, ribose, and —$CH_2$—O—CO—O-t-butyl; and $R_3$ is chosen from hydrogen; halogen; —NH-cyclopentyl; ethenylphenyl and ethynylphenyl, wherein the phenyl groups optionally are substituted with a $CF_3$ group; and an optionally substituted 5- or 6-membered aromatic or non-aromatic ring comprising 0, 1 or 2 hetero-atoms chosen from nitrogen, oxygen and sulfur.

3. The compound according to claim 1, wherein
$R_1$ comprises —[X—$(CH_2)_n]_m$—Y, wherein X is chosen from NH and oxygen, n is chosen from 1 and 2, m is chosen from 0 and 1, and Y is chosen from an optionally substituted 6-membered aromatic or non-aromatic ring comprising 0 or 1 N-atoms;

$R_2$ is chosen from hydrogen, methyl, ribose, and —$CH_2$—O—CO—O-t-butyl; and $R_3$ is chosen from hydrogen; halogen; —NH-cyclopentyl; ethenylphenyl and ethynylphenyl, wherein the phenyl groups optionally are substituted with a $CF_3$ group; and an optionally substituted 5- or 6-membered aromatic or non-aromatic ring comprising 0, 1 or 2 hetero-atoms chosen from nitrogen, oxygen and sulfur.

4. The compound according to claim 1, wherein
$R_1$ comprises —[X—$(CH_2)_n]_m$—Y, wherein X comprises NH, n is chosen from 1 and 2, m comprises 1, and Y comprises an optionally hydroxylated phenyl group;

$R_2$ is chosen from hydrogen, ribose and —$CH_2$—O—CO—O-t-butyl; and $R_3$ comprises hydrogen.

5. The compound according to claim 1, wherein the compound of formula (1) is chosen from:
2-nitro-6-trifluoromethyl-9-methyl purine,
2-morpholinyl-6-fluoromethyl-9-β-D-ribofuranosyl purine,
2-piperidinyl-6-trifluoromethyl-9-β-D-ribofuranosyl purine,
2-(4-OH-piperidinyl)-6-trifluoromethyl-9-β-D-ribofuranosyl purine,
2-(OH-ethyl-piperazinyl)-6-trifluoromethyl-9-β-D-ribofuranosyl purine,
6-trifluoromethyl-2-benzylamino purine,
6-trifluoromethyl-9-methyl-2-benzylamino purine,
2-benzylamino-6-trifluoromethyl-9-β-D-ribofuranosyl purine,
6-trifluoromethyl-2-phenethylamino purine,
6-trifluoromethyl-9-methyl-2-phenethylamino purine,
8-bromo-6-trifluoromethyl-9-methyl-2-phenethylamino purine,
8-iodo-6-trifluoromethyl-9-methyl-2-phenethylamino purine,
8-(furan-2-yl)-6-trifluoromethyl-9-methyl-2-phenethylamino purine,
8-(thien-2-yl)-6-trifluoromethyl-9-methyl-2-phenethylamino purine,
8-N-pyrrolidinyl-6-trifluoromethyl-9-methyl-2-phenethylamino purine,
8-N-piperidinyl-6-trifluoromethyl-9-methyl-2-phenethylamino purine,
8-N-morpholinyl-6-trifluoromethyl-9-methyl-2-phenethylamino purine,
8-cyclopentylamino-6-trifluoromethyl-9-methyl-2-phenethylamino purine, 8-phenyl-6-trifluoromethyl-9-methyl-2-phenethylamino purine,
8-(3-fluorophenyl)-6-trifluoromethyl-9-methyl-2-phenethylamino purine,
8-E-styryl-6-trifluoromethyl-9-methyl-2-phenethylamino purine,
8-Z-styryl-6-trifluoromethyl-9-methyl-2-phenethylamino purine,
8-phenylacetylene-6-trifluoromethyl-9-methyl-2-phenethylamino purine,
8-E-(4-trifluoromethylstyryl)-6-trifluoromethyl-9-methyl-2-phenethylamino purine,
8-Z-(4-trifluoromethylstyryl)-6-trifluoromethyl-9-methyl-2-phenethylamino purine,
2-phenethylamino-6-$CF_3$-9-β-D-ribofuranosyl purine,
2-(4-hydroxy-phenethylamino)-6-trifluoromethyl-9-β-D-ribo-furanosyl purine
6-trifluoromethyl-2-phenetylamino-9-BocOM-purine,
6-trifluoromethyl-2-benzylamino-9-BocOM-purine, and
2-phenethyloxy-6-trifluoromethyl-9-β-D-ribofuraflosyl purine.

6. A pharmaceutical composition comprising
at least one pharmaceutically acceptable component chosen from a carrier, an auxiliary substance, and any combination thereof, and
an effective amount of at least one compound of formula (1):

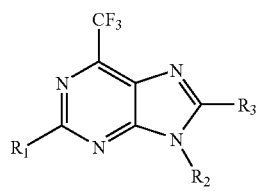

(1)

or a pharmaceutically acceptable salt, a tautomer, a stereoisomer, or a mixture of any of the foregoing wherein:
$R_1$ is chosen from —[X—$CH_2$)$_n$]$_m$—Y, wherein X is chosen from NH and oxygen, n is chosen from 0, 1, 2 and 3, m is chosen from 0 and 1, and Y is chosen from an optionally substituted 5- or 6-membered aromatic or non-aromatic ring comprising 0, 1 or 2 hetero-atoms chosen from N, O and S; and a nitro group;
$R_2$ is chosen from hydrogen, $C_{1-3}$-alkyl, ribose, —$CH_2$—O—CO—O-t-butyl, and aryl-($C_{1-3}$)alkyl; and
$R_3$ is chosen from hydrogen; halogen; $NH_2$; —NH—($C_{1-6}$)alkyl; —N-di($C_{1-6}$)alkyl; —NH-cyclo($C_{3-8}$)alkyl; $C_{2-4}$-alkenyl(hetero)aryl and $C_{2-4}$-alkynyl(hetero)aryl, wherein the hetero-atoms are chosen from N, O, and S and optionally, wherein the (hetero)aryl groups are optionally substituted; and an optionally substituted 5- or 6-membered aromatic or non-aromatic ring, comprising 0, 1 or 2 hetero-atoms chosen from nitrogen, oxygen and sulfur.

7. The composition according to claim 6, wherein in the at least one compound of formula (I):
$R_1$ is chosen from —[X—$CH_2$)$_n$]$_m$—Y, wherein X is chosen from NH and oxygen, n is chosen from 1 and 2, m is chosen 0 and 1, and Y is chosen from an optionally substituted 6-membered aromatic or non-aromatic ring comprising 0, 1 or 2 hetero-atoms chosen from N and O, or R; and a nitro group;

$R_2$ is chosen from hydrogen, methyl, ribose, and —$CH_2$—O—CO—O-t-butyl; and
$R_3$ is chosen from hydrogen; halogen; —NH-cyclopentyl; ethenylphenyl and ethynylphenyl, wherein the phenyl groups optionally are substituted with a $CF_3$ group; and an optionally substituted 5- or 6-membered aromatic or non-aromatic ring comprising 0, 1 or 2 hetero-atoms chosen from nitrogen, oxygen and sulfur.

8. The composition according to claim 6, wherein in the at least one compound of formula (I):
$R_1$ comprises —[X—$CH_2$)$_n$]$_m$—Y, wherein X is chosen from NH and oxygen, n is chosen from 1 and 2, m is chosen from 0 and 1, and Y is chosen from an optionally substituted 6-membered aromatic or non-aromatic ring comprising 0 or 1 N-atoms;
$R_2$ is chosen from hydrogen, methyl, ribose, and —$CH_2$—O—CO—O-t-butyl; and
$R_3$ is chosen from hydrogen; halogen; —NH-cyclopentyl; ethenylphenyl and ethynylphenyl, wherein the phenyl groups optionally are substituted with a $CF_3$ group; and an optionally substituted 5- or 6-membered aromatic or non-aromatic ring comprising 0, 1 or 2 hetero-atoms chosen from nitrogen, oxygen and sulfur.

9. The composition according to claim 6, wherein in the at least one compound of formula (I):
$R_1$ comprises —[X—$CH_2$)$_n$]$_m$—Y, wherein X comprises NH, n is chosen from 1 and 2, m comprises 1, and Y comprises an optionally hydroxylated phenyl group;
$R_2$ is chosen from hydrogen, ribose and —$CH_2$—O—CO—O-t-butyl; and
$R_3$ comprises hydrogen.

10. The composition according to claim 6, wherein the at least one auxiliary substance is chosen from magnesium carbonate, titanium dioxide, lactose, mannitol and other sugars or sugar alcohols, talc, lactoprotein, gelatin, starch, cellulose and derivatives thereof, animal and vegetable oils, solvents, and any combination thereof.

11. The composition according to claim 6, wherein the composition is in a form chosen from solutions, powders, tablets, capsules, ointments, and suppositories.

12. A method of preparing a pharmaceutical composition comprising combining an effective amount of at least one compound of formula (1):

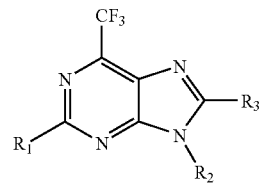

(1)

or a pharmaceutically acceptable salt, a tautomer, a stereoisomer, or a mixture of any of the foregoing wherein:
$R_1$ is chosen from —[X—$CH_2$)$_n$]$_m$—Y, wherein X is chosen from NH and oxygen, n is chosen from 0, 1, 2 and 3, m is chosen from 0 and 1, and Y is chosen from an optionally substituted 5- or 6-membered aromatic or non-aromatic ring comprising 0, 1 or 2 hetero-atoms chosen from N, O and S; and a nitro group;
$R_2$ is chosen from hydrogen, $C_{1-3}$-alkyl, ribose, —$CH_2$—O—CO—O-t-butyl, and aryl-($C_{1-3}$)alkyl; and
$R_3$ is chosen from hydrogen; halogen; $NH_2$; —NH—($C_{1-6}$)alkyl; —N-di($C_{1-6}$)alkyl; —NH-cyclo($C_{3-8}$)alkyl;

$C_{2-4}$-alkenyl(hetero)aryl and $C_{2-4}$-alkynyl(hetero)aryl, wherein the hetero-atoms are chosen from N, O, and S and optionally, wherein the (hetero)aryl groups are substituted; and an optionally substituted 5- or 6-membered aromatic or non-aromatic ring, comprising 0, 1 or 2 hetero-atoms chosen from nitrogen, oxygen and sulfur; and at least one pharmaceutically acceptable component chosen from a carrier, an auxiliary substance, and any combination thereof.

13. A compound of formula (2a):

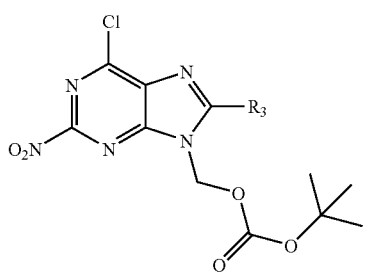

(2a)

wherein the compound of formula (2a) is used in synthesizing at least one compound of formula (1) and $R_3$ is chosen from hydrogen; halogen; $NH_2$; —NH—($C_{1-6}$)alkyl; —N-di($C_{1-6}$)alkyl; —NH-cyclo($C_{3-8}$)alkyl; $C_{2-4}$-alkenyl(hetero)aryl and $C_{2-4}$-alkynyl(hetero)aryl, wherein the hetero-atoms are chosen from N, O, and S and optionally, wherein the (hetero)aryl groups are substituted; and an optionally substituted 5- or 6-membered aromatic or non-aromatic ring comprising 0, 1 or 2 hetero-atoms chosen from nitrogen, oxygen and sulfur.

14. A compound of formula (2b):

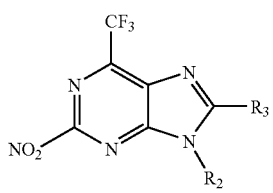

(2b)

wherein $R_2$ is chosen from hydrogen, $C_{1-3}$-alkyl, ribose, —$CH_2$—O—CO—O-t-butyl, and aryl-($C_{1-3}$)alkyl, and $R_3$ is chosen from hydrogen; halogen; $NH_2$; —NH—($C_{1-6}$)alkyl; —N-di($C_{1-6}$)alkyl; —NH-cyclo($C_{3-8}$)alkyl; $C_{2-4}$-alkenyl(hetero)aryl and $C_{2-4}$-alkynyl(hetero)aryl, wherein the hetero-atoms are chosen from N, O, and S and optionally, wherein the (hetero)aryl groups are substituted; and an optionally substituted 5- or 6-membered aromatic or non-aromatic ring, comprising 0, 1 or 2 hetero-atoms chosen from nitrogen, oxygen and sulfur, wherein the compound of formula (2b) is used in synthesizing at least one compound of formula (1).

15. A method for preparing a compound according to formula (1) comprising:

(a) conducting a trifluoromethylation of a compound of formula (3):

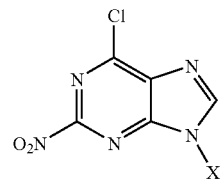

(3)

wherein X Is chosen from tri-O-acetate-ribose, methyl, and —$CH_2$—O—C(O)O-tBu to obtain in a compound of formula (4):

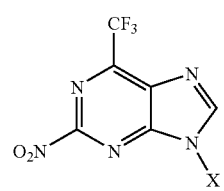

(4)

(b) substituting by nucleophilic substitution at the nitro group of compound (4) to yield a compound of formula (5):

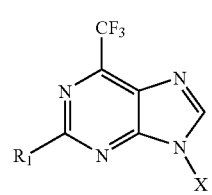

(5)

wherein $R_1$ is chosen from —$[X—CH_2)_n]_m$—Y, wherein X is chosen from NH and oxygen, n is chosen from 0, 1, 2 and 3, m is chosen from 0 and 1, and Y is chosen from an optionally substituted 5- or 6-membered aromatic or non-aromatic ring comprising 0, 1 or 2 hetero-atoms chosen from N, O and S; and a nitro group, and, (c1) wherein X comprises tri-O-ecetate, the next step of the method being chosen from hydrolyzing the compound of formula (5) to yield a corresponding compound of formula (1) with a 9-ribose substituent:

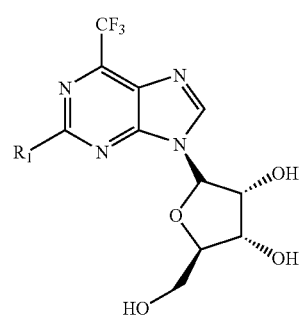

and (c2) treating the product with a strong organic acid to yield a compound of formula (6):

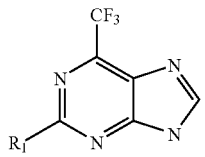

(6)

or (c3): wherein X comprises —CH$_2$—O—C(O)O-tBu, treating the compound of formula (5) with a strong base to yield a compound of formula (6), (d) alkylating the compound of formula (6) to yield a compound of the formula (7):

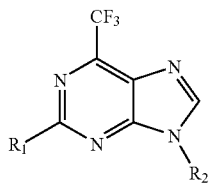

(7)

wherein: R$_1$ is chosen from —[X—CH$_2$)$_n$]$_m$—Y, wherein X is chosen from NH and oxygen, n is chosen from 0, 1, 2 and 3, m is chosen from 0 and 1, and Y is chosen from an optionally substituted 5 or 6-membered aromatic or non-aromatic ring comprising 0, 1 or 2 hetero-atoms chosen from N, O and S; and a nitro group, (e) halogenating the compound of formula (7) to yield a compound of formula (8):

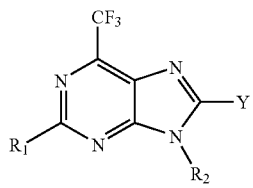

(8)

wherein Y is chosen from bromine and iodine, and (f) conducting an amination or an alkylation to result in a compound of formula (1):

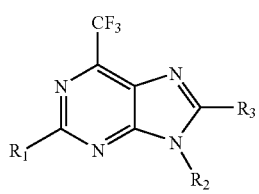

(1)

wherein:

R$_1$ is chosen from —[X—CH$_2$)$_n$]$_m$—Y, wherein X is chosen from NH and oxygen, n is chosen from 0, 1, 2 and 3, m is chosen from 0 and 1, and Y is chosen from an optionally substituted 5- or 6-membered aromatic or non-aromatic ring comprising 0, 1 or 2 hetero-atoms chosen from N, O and S; and a nitro group;

R$_2$ is chosen from hydrogen, C$_{1-3}$-alkyl, ribose, —CH$_2$—O—CO—O-t-butyl, and aryl-(C$_{1-3}$)alkyl; and R$_3$ is chosen from hydrogen; halogen; NH$_2$; —NH—(C$_{1-6}$)alkyl; —N-di(C$_{1-6}$)alkyl; —NH-cyclo(C$_{3-8}$)alkyl; C$_{2-4}$-alkenyl(hetero)aryl and C$_{2-4}$-alkynyl(hetero)aryl, wherein the hetero-atoms are chosen from N, O, and S and optionally, wherein the (hetero)aryl groups are substituted; and an optionally substituted 5- or 6-membered aromatic or non-aromatic ring, comprising 0, 1 or 2 hetero-atoms chosen from nitrogen, oxygen and sulfur.

* * * * *

UNITED STATES PATENT AND TRADEMARK OFFICE
CERTIFICATE OF CORRECTION

PATENT NO.       : 7,371,737 B2
APPLICATION NO.  : 11/219818
DATED            : May 13, 2008
INVENTOR(S)      : Melle Koch et al.

It is certified that error appears in the above-identified patent and that said Letters Patent is hereby corrected as shown below:

In claim 2, column 25, line 66, "-[X-CH$_2$)$_n$]$_m$-Y," should read -- -[X-(CH$_2$)$_n$]$_m$-Y,--.

In claim 5, column 27, lines 16-17, "2-(4-hydroxy-phenethylamino)-6-trifluoromethyl-9-β-D-ribo-furanosyl purine" should read --2-(4-hydroxy-phenethylamino)-6-trifluoromethyl-9-β-D-ribofuranosyl purine,--.

In claim 5, column 27, line 18, "6-trifluoromethyl-2-phenetylamino-9-BocOM-purine," should read --6-trifluoromethyl-2-phenethylamino-9-BocOM-purine,--.

In claim 5, column 27, line 20, "2-phenethyloxy-6-trifluoromethyl-9-β-D-ribofuraflosyl" should read --2-phenethyloxy-6-trifluoromethyl-9-β-D-ribofuranosyl--.

In claim 6, column 27, line 43, "-[X-CH$_2$)$_n$]$_m$-Y," should read -- -[X-(CH$_2$)$_n$]$_m$-Y,--.

In claim 7, column 27, line 61, "formula (I):" should read --formula (1):--.

In claim 7, column 27, line 62, "-[X-CH$_2$)$_n$]$_m$-Y," should read -- -[X-(CH$_2$)$_n$]$_m$-Y,--.

In claim 7, column 27, line 64, "chosen 0" should read --chosen from 0--.

In claim 8, column 28, line 10, "formula (I):" should read --formula (1):--.

In claim 9, column 28, line 25, "formula (I):" should read --formula (1):--.

In claim 15, column 30, line 12, "Is" should read --is--.

In claim 15, column 30, line 40, "-[X-CH$_2$)$_n$]$_m$-Y," should read -- -[X-(CH$_2$)$_n$]$_m$-Y,--.

In claim 15, column 30, line 46, "tri-O-ecetate," should read --tri-O-acetate,--.

In claim 15, column 31, line 36, "-[X-CH$_2$)$_n$]$_m$-Y," should read -- -[X-(CH$_2$)$_n$]$_m$-Y,--.

In claim 15, column 31, lines 39-40, "5 or" should read --5- or--.

UNITED STATES PATENT AND TRADEMARK OFFICE
CERTIFICATE OF CORRECTION

PATENT NO. : 7,371,737 B2
APPLICATION NO. : 11/219818
DATED : May 13, 2008
INVENTOR(S) : Melle Koch et al.

It is certified that error appears in the above-identified patent and that said Letters Patent is hereby corrected as shown below:

In claim 15, column 32, line 27, "-$[X-CH_2)_n]_m$-Y," should read -- -$[X-(CH_2)_n]_m$-Y,--.

Signed and Sealed this

Twenty-sixth Day of August, 2008

JON W. DUDAS
*Director of the United States Patent and Trademark Office*